United States Patent
Chiao

(10) Patent No.: US 11,247,049 B2
(45) Date of Patent: Feb. 15, 2022

(54) WIRELESS TISSUE STIMULATION DEVICES

(71) Applicant: Board of Regents, The University of Texas System, Austin, TX (US)

(72) Inventor: Jung-Chih Chiao, Grand Prairie, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 280 days.

(21) Appl. No.: 16/218,729

(22) Filed: Dec. 13, 2018

(65) Prior Publication Data

US 2019/0111254 A1 Apr. 18, 2019

Related U.S. Application Data

(63) Continuation of application No. 15/022,382, filed as application No. PCT/US2014/056912 on Sep. 23, 2014, now Pat. No. 10,213,599.

(60) Provisional application No. 61/881,382, filed on Sep. 23, 2013.

(51) Int. Cl.
   *A61N 1/36*     (2006.01)
   *A61N 1/375*    (2006.01)
   *A61N 1/378*    (2006.01)
   *A61N 1/05*     (2006.01)
   *A61N 1/372*    (2006.01)

(52) U.S. Cl.
   CPC ....... *A61N 1/36007* (2013.01); *A61N 1/0509* (2013.01); *A61N 1/3756* (2013.01); *A61N 1/3787* (2013.01); *A61N 1/37223* (2013.01); *A61N 1/3727* (2013.01); *A61N 1/37264* (2013.01)

(58) Field of Classification Search
   USPC ......................................... 607/40
   See application file for complete search history.

(56) References Cited

U.S. PATENT DOCUMENTS

| | | | |
|---|---|---|---|
| 6,475,136 B1 * | 11/2002 | Forsell | A61F 2/0036 600/37 |
| 2008/0195171 A1 * | 8/2008 | Sharma | A61N 1/0507 607/40 |
| 2011/0087337 A1 * | 4/2011 | Forsell | A61F 2/004 623/23.68 |

* cited by examiner

*Primary Examiner* — Nicole F Lavert
(74) *Attorney, Agent, or Firm* — Nexsen Pruet, PLLC

(57) ABSTRACT

In one aspect, wireless gastrointestinal stimulations are described herein. In some embodiments, a system described herein comprises at least one transmitter and at least one stimulation device. The transmitter can include a signal generator operable to generate an electromagnetic signal, a first antenna operable to broadcast the electromagnetic signal, and an energy source. The at least one stimulation device is operable to deliver a pattern of electrical pulses to a gastrointestinal tissue comprising a muscle, and the stimulation device includes a circuit board having a circumference, at least one second antenna wrapped around the circumference of the circuit board, the at least one second antenna being configured to receive the electromagnetic signal and to generate an electrical current from the electromagnetic signal, and at least one electrode operable to deliver the electrical current to the muscle.

20 Claims, 11 Drawing Sheets

WIRELESS TISSUE STIMULATION DEVICES

CROSS REFERENCE TO RELATED APPLICATIONS

The present application is a continuation of U.S. patent application Ser. No. 15/022,382, filed Mar. 16, 2016, which is a U.S. national stage application under 35 U.S.C. § 371 of International Application No. PCT/US2014/056912, filed Sep. 23, 2014, which claims priority pursuant to 35 U.S.C. § 119 to U.S. Patent Application Ser. No. 61/881,382 filed Sep. 23, 2013, each of which is hereby incorporated by reference in its entirety.

FIELD

The present invention relates to wireless tissue stimulation devices and, in particular, to devices and systems for stimulating muscular and/or gastrointestinal tissue.

BACKGROUND

Gastric dysmotility disorders such as gastroparesis can cause chronic debilitating symptoms. Patients suffering from such disorders generally suffer from incomplete gastric emptying and gastric dysrhythmia. In some cases, electrical stimulation can be used to treat gastric dysmotility disorders. However, some currently existing electrical stimulation devices suffer from one or more disadvantages. For example, some previous devices are bulky and/or exhibit limited performance lifetimes. Such devices can require recurring invasive surgeries to place and/or replace the devices. In addition, some existing devices provide only a single operation mode, such that electrical stimulation cannot be adjusted by a patient or doctor during use. Thus, there is a need for improved muscular and/or gastrointestinal stimulation devices.

Further, obesity and associated symptoms can often result in the necessity of surgical intervention for treatment. Patients requiring surgical intervention generally require highly invasive procedures such as restrictive or malabsorptive surgeries to reduce the size of digestive organs, to slow digestion, or to otherwise alter normal digestive function. In many cases, such invasive procedures can result in one or more serious side effects. Thus, there is a need for improved devices and or methods for treating obesity in patients.

SUMMARY

In one aspect, wireless tissue stimulation devices and systems are described herein which, in some embodiments, can provide one or more advantages compared to other devices and systems. For instance, in some cases, a device or system described herein can have a small device size and/or form factor. Such a device, in some instances, can deliver a pattern of electrical pulses to muscle or gastrointestinal tissue while maintaining a cross-sectional diameter small enough to facilitate implantation of the device, including in a submucosal region of a patient's body. A device or system described herein can also be wirelessly powered and/or wirelessly rechargeable. Moreover, in some embodiments, a device or system described herein can be reconfigurable, including during use in vivo.

A wireless tissue stimulation device described herein, in some cases, comprises a wirelessly powered or a wirelessly rechargeable muscular stimulation device. Such a device, in some embodiments, comprises a circuit board having a circumference and at least one antenna wrapped around the circumference of the circuit board. The at least one antenna, which may be formed from or defined by metal wire, is configured to receive an electromagnetic signal and to generate an electrical current from the electromagnetic signal. Additionally, the device further comprises at least one electrode operable to deliver the electrical current to a muscle. In some instances, the device comprises at least two electrodes. In some such embodiments, at least two electrodes can be located on opposing ends of the device and/or can be generally loop-shaped. Moreover, in some embodiments, a device described herein also comprises at least one rechargeable battery and a switch operable to switch the device between a battery recharging mode and an operation mode. Further, in some cases, a circuit board, antenna, rechargeable battery, and/or switch of a wireless tissue stimulation device described herein can be coated with a biocompatible polymer.

In other embodiments, a wireless stimulation device described herein comprises a flexible or foldable substrate, wherein at least one antenna is disposed on the flexible or foldable substrate and is configured to receive an electromagnetic signal and to generate an electrical current from the electromagnetic signal. The device can also comprise a circuit disposed on the flexible or foldable substrate, the circuit comprising a capacitor, an inductor, and a controller. Additionally, in some cases, a device described herein further comprises one or more electrodes operable to deliver the electrical current to a muscle in contact with a top surface of the device and/or a bottom surface of the device. Further, in some embodiments, a device described herein also comprises a pH detector and/or a strain detector. Moreover, in some instances, a device described herein further comprises a flexible or foldable superstate in facing opposition to the flexible or foldable substrate of the device. Additionally, in some cases, one or more of the flexible or foldable substrate, the flexible or foldable superstrate, the at least one antenna, and the circuit of a device described herein are coated with a biocompatible polymer. Moreover, in some instances, a wirelessly powered muscular stimulation device described herein does not comprise a battery.

In another aspect, tissue stimulation systems are described herein. In some embodiments, such a system comprises at least one transmitter and at least one stimulation device. The transmitter can include a signal generator operable to generate an electromagnetic signal, a first antenna operable to broadcast the electromagnetic signal, and an energy source. Additionally, in some instances, the transmitter further comprises an amplifier. The stimulation device of the system can comprise any tissue stimulation device described hereinabove. Further, it is to be understood that the at least one stimulation device is operable to deliver a pattern of electrical pulses to a gastrointestinal tissue comprising a muscle. In some cases, for instance, the stimulation device includes a circuit board having a circumference and at least one second antenna wrapped around the circumference of the circuit board. The at least one second antenna is configured to receive the electromagnetic signal and to generate an electrical current from the electromagnetic signal. The stimulation device further comprises at least one electrode operable to deliver the electrical current to the muscle. Further, in certain embodiments, the stimulation device of a system described herein does not comprise a battery.

Moreover, in some cases, a system described herein can comprise more than one stimulation device. In some instances, a system described herein comprises at least two stimulation devices, and the at least two stimulation devices are operable to deliver at least two patterns of electrical pulses to gastrointestinal or other tissue. The two patterns can be the same or can differ from one another.

In yet another aspect, methods of electrically stimulating gastrointestinal tissue in a patient are described herein. A method of electrically stimulating gastrointestinal tissue in a patient, in some embodiments, comprises implanting at least one stimulation device in the patient. The stimulation device can comprise any tissue stimulation device described hereinabove. For example, in some cases, the at least one stimulation device comprises at least one antenna configured to receive electromagnetic signals and to generate electrical current from the electromagnetic signals, and at least one electrode operable to deliver electrical current to the patient. Thus, a method described herein can further comprise transmitting an electromagnetic signal from a transmitter, such as a transmitter described hereinabove; receiving the electromagnetic signal with an antenna of the stimulation device; generating an electrical current from the received electromagnetic signal; and delivering the electrical current to the patient through one or more electrodes of the stimulation device. Additionally, in some embodiments wherein the stimulation device comprises a rechargeable battery, a method described herein can further comprise delivering the electrical current to the rechargeable battery after generating the electrical current in a recharging mode of the stimulation device, and delivering the electrical current from the rechargeable battery to the electrode in a stimulation mode of the device. Further, in some such cases, the method can also comprise actuating a switch to switch between the recharging mode and the stimulation mode of the stimulation device. Moreover, in some embodiments, the transmitter used in a method described herein is external to the patient. In addition, a method of electrically stimulating gastrointestinal tissue described herein, in some cases, can be used to treat obesity and/or control appetite, including by inducing nausea in a patient through the electrical stimulation of the gastrointestinal tissue. A method of electrically stimulating gastrointestinal tissue described herein can also be used to increase or decrease gastric motility. Thus, in some instances, a method described herein can be used to treat gastroparesis or other dysmotility disorders.

In still another aspect, methods of reconfiguring a wireless stimulation device are described herein. Such methods can be utilized with devices having a resonant circuit operable to receive an electromagnetic signal transmitted within a carrier frequency range having a resonant frequency, including devices described hereinabove. A method of reconfiguring a wireless stimulation device, in some embodiments, comprises transmitting a mode change signal to the device, transmitting a first data signal to the device, the first data signal comprising a first bit signal or a second bit signal, and transmitting a first confirmation signal to the device. The mode change signal has a frequency within a first band within the carrier frequency range, the first bit signal has a frequency within a second band within the carrier frequency range, the second bit signal has a frequency within a third band within the carrier frequency range, and the first confirmation signal has a frequency within a fourth band within the carrier frequency range. Further, in some cases, the power transfer efficiencies of the mode change signal, first data signal, and the first confirmation signal vary less than 1% from a power transfer efficiency of the resonant frequency. Moreover, in some instances, the method further comprises transmitting a second data signal and transmitting a second confirmation signal. In some cases, the first data signal and the second data signal are the same. Alternatively, in other cases, the first data signal and the second data signal are different. Further, in some embodiments, the carrier frequency range spans less than about 50 kHz. In some instances, the carrier frequency range is about 1.28 MHz to about 1.32 MHz or about 1.25 MHz to about 1.29 MHz.

These and other embodiments are described in more detail in the detailed description which follows.

DETAILED DESCRIPTION

Embodiments described herein can be understood more readily by reference to the following detailed description, examples, and drawings. Elements, apparatus and methods described herein, however, are not limited to the specific embodiments presented in the detailed description, examples, and drawings. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" should generally be considered to include the end points 5 and 10.

I. Wireless Muscular Stimulation Devices

In one aspect, wireless muscular stimulation devices are described herein which, in some embodiments, demonstrate a small size, flexible or foldable form factor, wireless operability, and/or wireless reconfigurability. Further, such wireless muscular stimulation devices can be operable as wirelessly rechargeable muscular stimulation devices and/or wirelessly powered stimulation devices.

Figure 1:
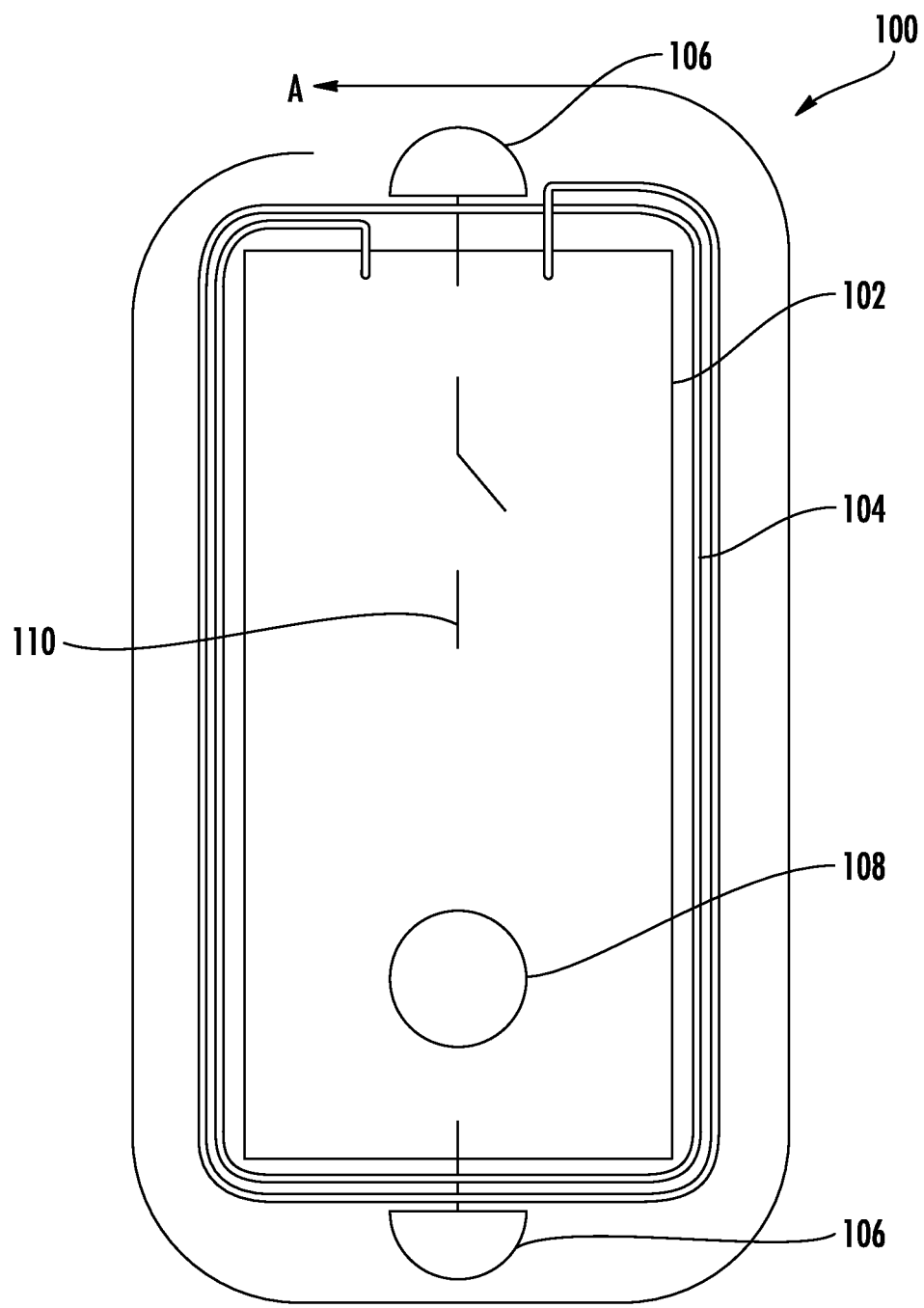
FIG. 1 illustrates a schematic diagram of a wireless stimulation device according to one embodiment described herein.

Turning now to specific embodiments, a wireless muscular stimulation device described herein, in some cases, is operable as a wirelessly rechargeable muscular stimulation device. With specific reference to FIGS. 1, 2A, and 2B, there is illustrated a wirelessly rechargeable muscular stimulation device (100), in accordance with one embodiment described herein. As illustrated in FIG. 1, wirelessly rechargeable muscular stimulation device (100) comprises a circuit board (102) having a circumference and at least one antenna (104) wrapped around the circumference of the circuit board (102). The antenna (104), in some cases, can be formed from or defined by a metal wire and can be wrapped around the circumference of the circuit board (102) any desired number of times, such as once or more than once. Such a looped antenna (104) is thus configured to receive an electromagnetic signal and to generate an electrical current from the electromagnetic signal. The device (100) further comprises electrodes (106). As illustrated in FIG. 1, the electrodes (106) are generally loop-shaped and are disposed on opposing ends of the device (100). However, other electrode shapes and configurations are also possible, as described further hereinbelow. Further, the electrodes (106) are operable to deliver electrical current to a muscle, such as a muscle in direct physical contact with one or both of the electrodes (106). The device (100) of FIG. 1 also comprises a rechargeable battery (108) and a switch (110) operable to switch between a battery recharging mode and an operation or stimulation mode of the device (100).

Figure 2A:
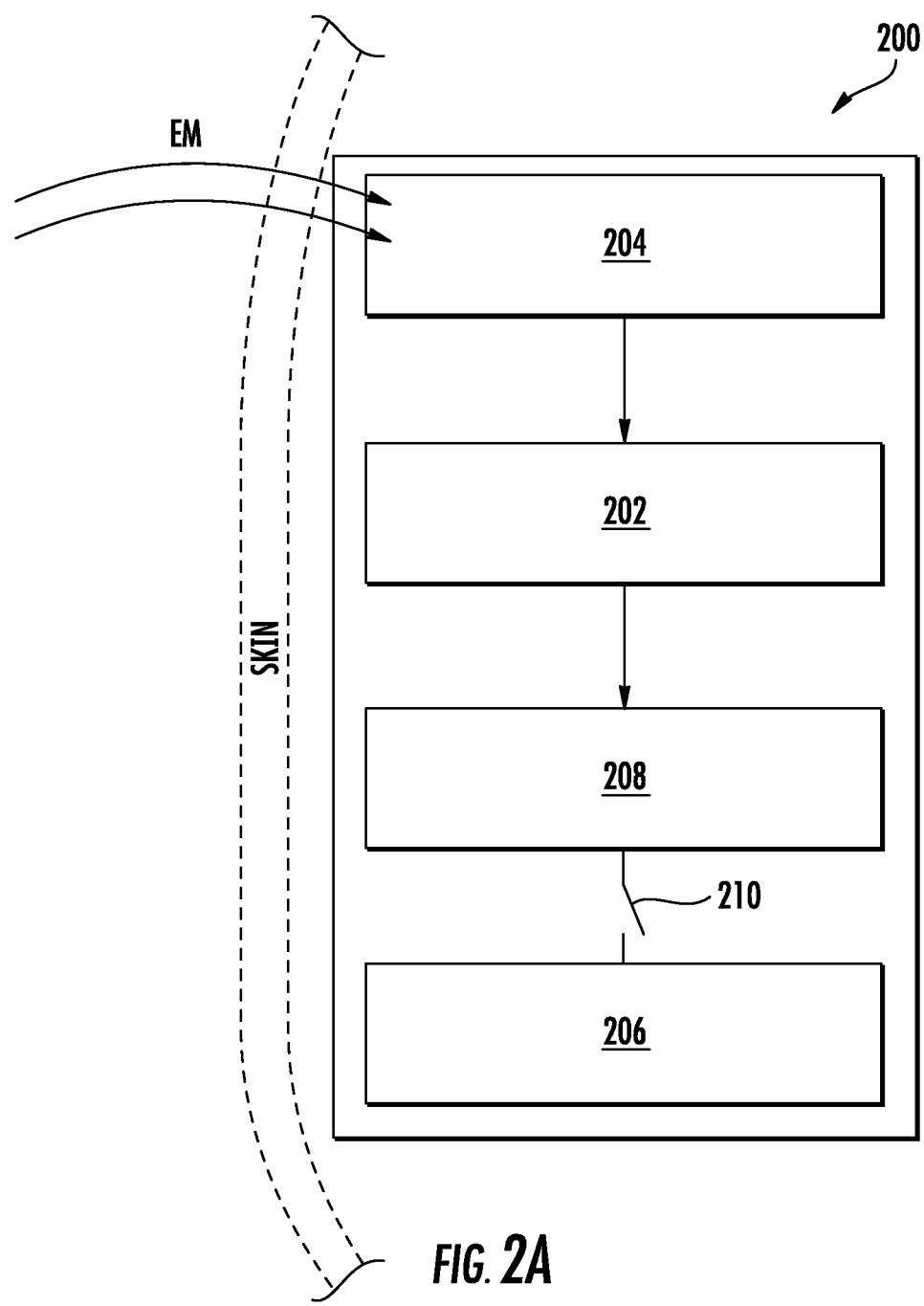
FIGS. 2A and 2B each illustrate a schematic diagram of a wireless stimulation device according to one embodiment described herein.
Figure 2B:
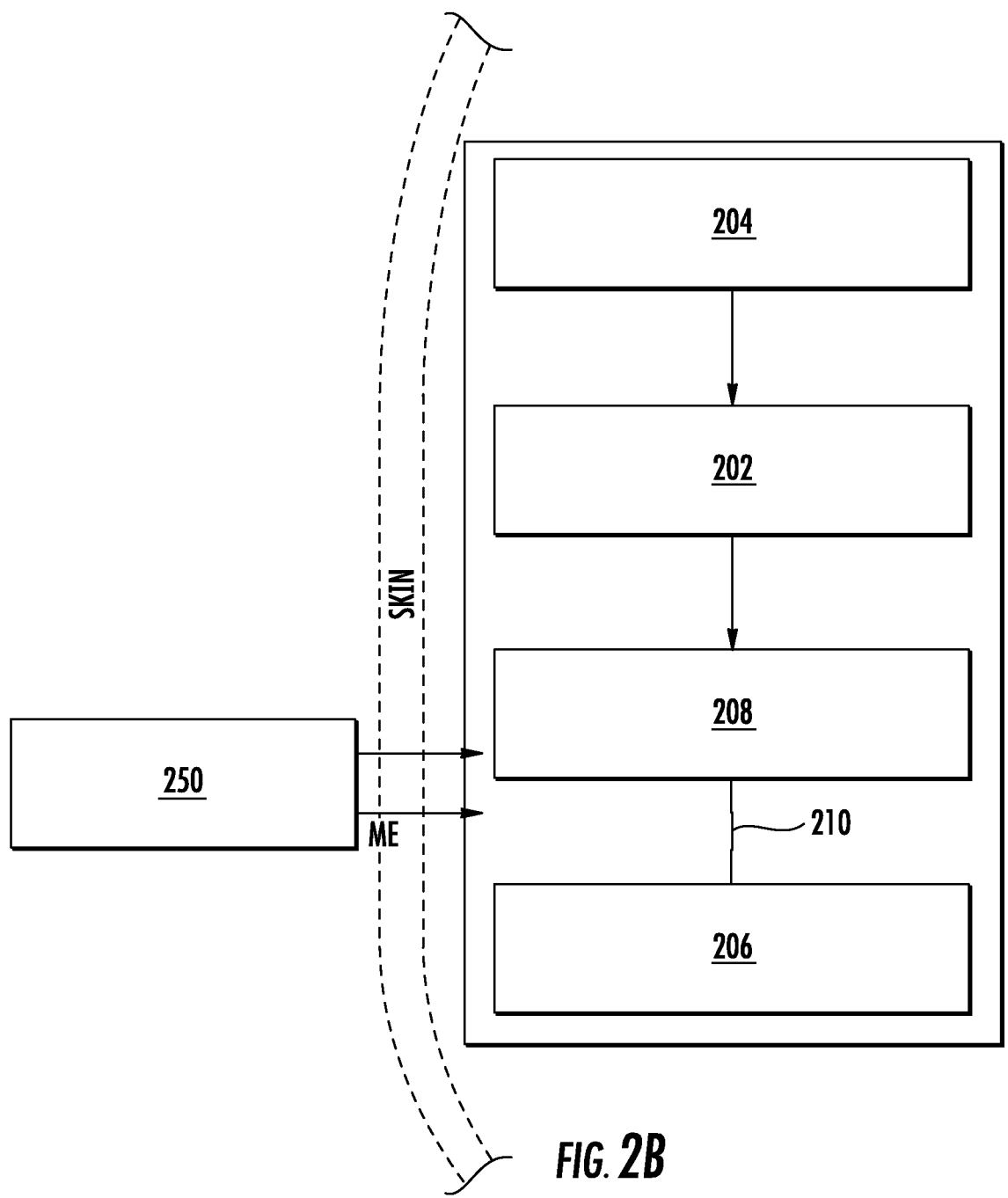

FIGS. 2A and 2B schematically illustrate the operation of a wirelessly rechargeable muscular stimulation device described herein in a recharging mode and a stimulation mode. As illustrated in FIG. 2A, the wirelessly rechargeable device (200) is operable to receive an electromagnetic signal (EM) using an antenna (204). The antenna (204) can generate an electrical current from the electromagnetic signal (EM) and transfer the electrical current to the circuit board (202), as illustrated schematically in FIGS. 2A and 2B by the arrow connecting the schematic representations of the antenna (204) and the circuit board (202). The circuit board (202) may comprise a charging circuit (not shown). Further, in the embodiment of FIGS. 2A and 2B, the circuit board (202) is electrically connected to at least one rechargeable battery (208), as illustrated schematically by the arrow connecting the schematic representations of the circuit board (202) and the at least one rechargeable battery (208). The rechargeable battery (208) is further electrically connected to at least one electrode (206) through a switch (210), as illustrated by the open (FIG. 2A) or closed (FIG. 2B) lines connecting the schematic illustrations of the rechargeable battery (208) and the at least one electrode (206). When the switch (210) is in an open position, as in FIG. 2A, current generated by the antenna (204) is prevented from being transferred to the at least one electrode (206), and can instead be utilized to charge the at least one rechargeable battery (208). When the switch (210) is closed, as in FIG. 2B, the electrical current generated by the antenna (204) and/or stored by the rechargeable battery (208) can be transferred to the at least one electrode (206). The electrode (206) can, in turn, deliver the electrical current to a muscle to provide electrical stimulation of the muscle. In some embodiments, as in FIG. 2B, the switch (210) is a magnetic reed switch which can be actuated between an open position (associated with a recharging mode) and a closed position (associated with a stimulation mode). In such embodiments, a magnet (250) can be used to operate the switch. In some cases, the magnet (250) can be located outside of or external to the patient, permitting external switching between a recharging mode and a stimulation mode of the device (200). As illustrated in FIG. 2B, the externally provided magnet (250) provides a magnetic signal (ME) through the skin of a patient in which the device (200) has been implanted.

A wireless tissue stimulation device described herein can also be operable as a wirelessly powered muscular stimulation device. Such a device may not comprise a battery or a switch described above. For example, in some cases, the stimulation device comprises a circuit board having a circumference, at least one antenna wrapped around the circumference of the circuit board, the at least one antenna being configured to receive an electromagnetic signal and to generate an electrical current from the electromagnetic signal, and at least one electrode operable to deliver the electrical current to a muscle.

Figure 3A:
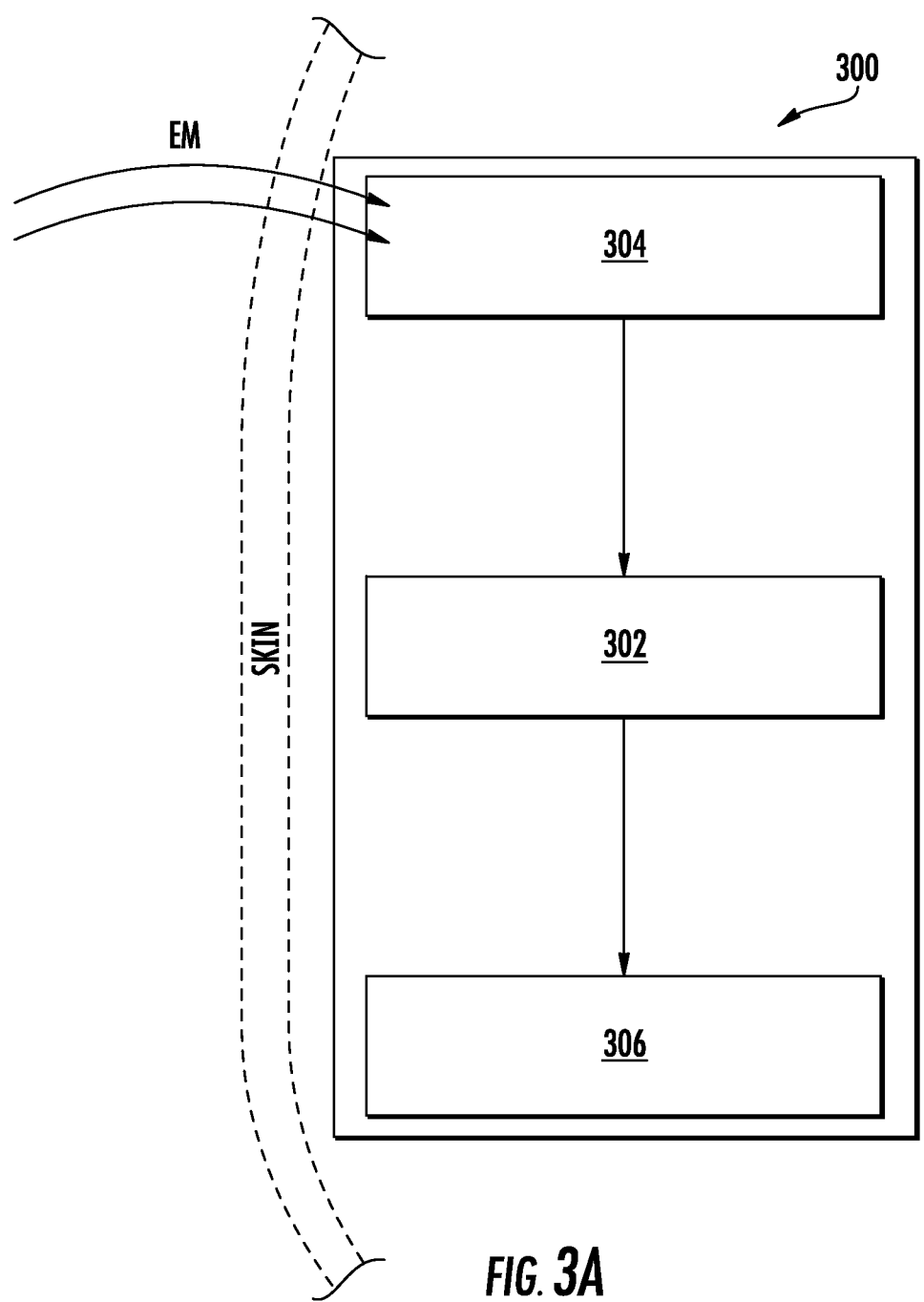
FIG. 3A illustrates a schematic diagram of a wireless stimulation device according to one embodiment described herein.
Figure 3B:
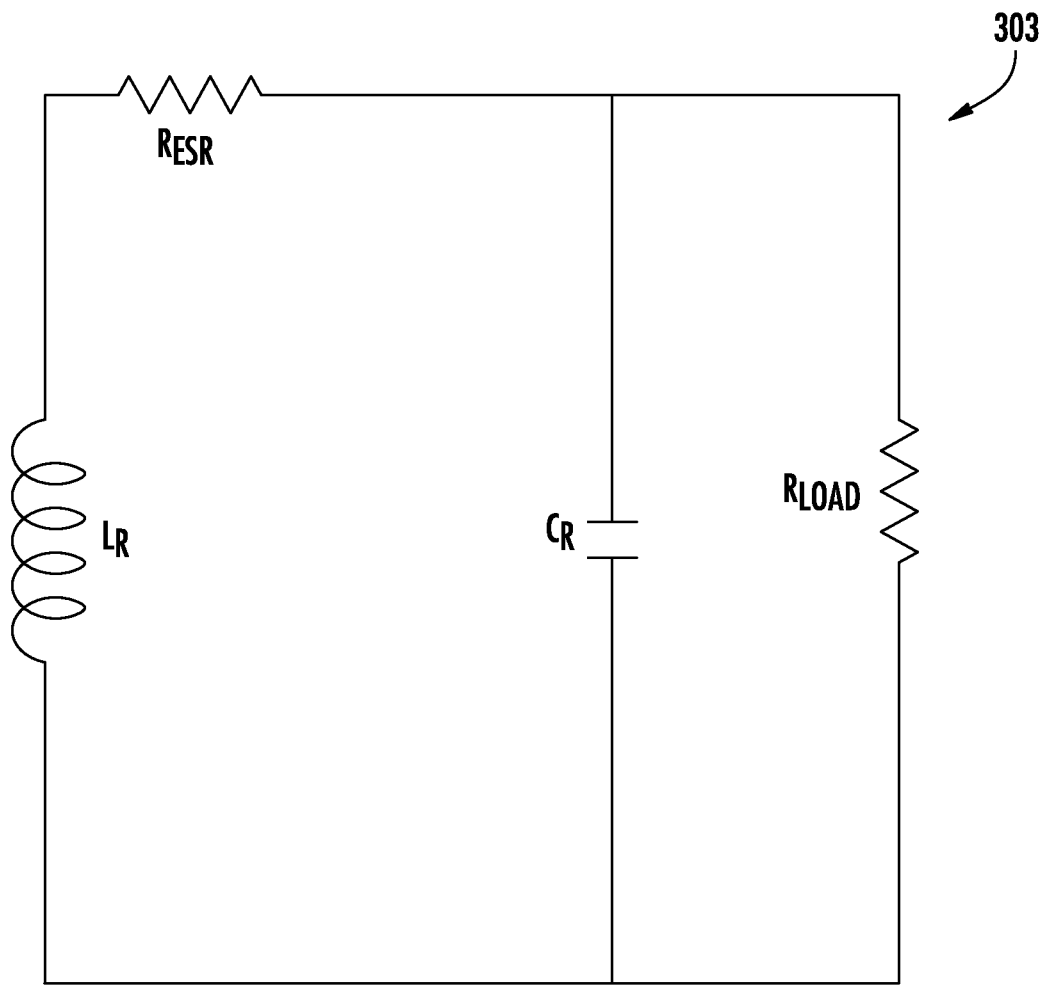
FIG. 3B illustrates a circuit diagram of a wireless stimulation device according to one embodiment described herein.

With specific reference to FIGS. 3A and 3B, there is illustrated a wirelessly powered muscular stimulation device (300). The wirelessly powered muscular stimulation device (300) illustrated in FIG. 3A comprises a circuit board (302) having a circumference, at least one antenna (304) wrapped around the circumference, and at least one electrode (306) operable to deliver electrical current to a muscle. In the embodiment illustrated in FIG. 3A, the circuit board (302) comprises an energy harvesting circuit (303). An illustration of one embodiment of an energy harvesting circuit (303) is provided in FIG. 3B. Symbols, designators, and nomenclature utilized herein in circuit diagrams, such as in FIG. 3B, generally conform to ASME standard ASME Y14.44-2008 Reference Designations for Electrical and Electronic Parts and Equipment. An inductor-capacitor LC can be arranged in series and tuned to a resonant frequency within a carrier frequency band. The inductor is generally designated $L_R$, and the capacitor is designated $C_R$. $R_{load}$ represents the load across the at least one electrode (306) when placed in contact with gastrointestinal tissue within a patient. $R_{ESR}$ represents the equivalent series resistance. It is to be understood that the energy harvesting circuit (303) of FIG. 3B can also be represented without illustrating $R_{ESR}$ as a separate component of the circuit.

In certain embodiments, a particular form factor or structure may be selected for its suitability for one or more methods of device implantation described hereinbelow. For example, in some cases, a capsule shaped device or circuit board may be used in order to facilitate implantation of the device endoscopically to place at least a portion of the device, such as at least one electrode, in contact with a mucosal layer of gastrointestinal tissue. Further, in certain embodiments, a device comprising a flexible or foldable substrate and/or superstrate may be sized, shaped, or otherwise configured to facilitate implantation of the device within, beneath, or between a mucosal layer, submucosal layer, serosal layer, and/or sublayers of a mucosal, submucosal, or serosal layer.

Figure 4A:
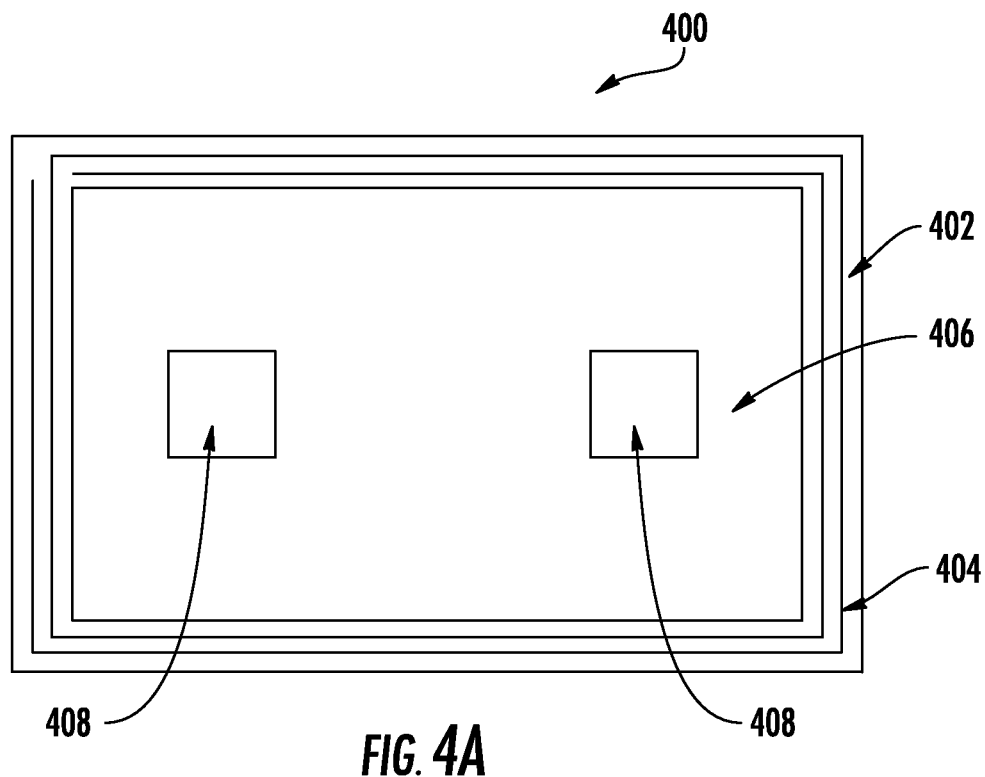
FIG. 4A illustrates a schematic diagram of a top view of a wireless stimulation device according to one embodiment described herein.
Figure 4B:
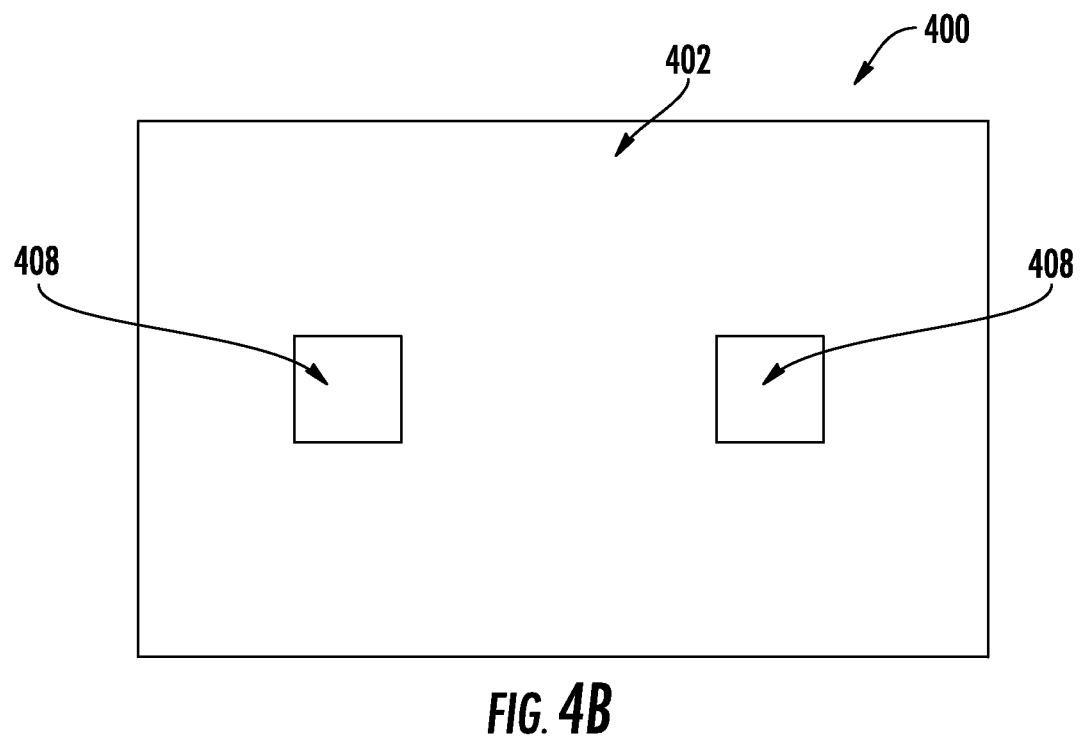
FIG. 4B illustrates a schematic diagram of a bottom view of the wireless stimulation device of FIG. 4A.

In addition, as described further herein, a tissue stimulation device may also have other form factors or structures. For example, a wirelessly powered muscular stimulation device described herein can be a flexible, foldable, or deformable device. With reference to FIGS. 4A and 4B, a device (400) can comprise a flexible or foldable substrate (402), at least one antenna (404) disposed on or defined by the flexible or foldable substrate (402), a circuit (406) disposed on or defined by the flexible or foldable substrate (402), and one or more electrodes (408). The antenna (404) can be configured to receive an electromagnetic signal and then generate an electrical current from the electromagnetic signal. The electrodes (408) can be configured to deliver the electrical current to a muscle in contact with a top surface of the device (400) and/or a bottom surface of the device (400). In some instances, the electrodes (408) can deliver the electrical current to the muscle through both the top surface and the bottom surface of the device (400) simultaneously or substantially simultaneously. The circuit (406), in some cases, can comprise a capacitor (not shown), an inductor (not shown), and a controller (not shown). Other circuit components can also be used. Moreover, in some cases, one or more components of a circuit (406) can be surface mounted components, which may or may not be soldered to the flexible or foldable substrate (402). FIG. 4A illustrates a top view of the device (400), and FIG. 4B illustrates a bottom view of the device (400).

Figure 5A:
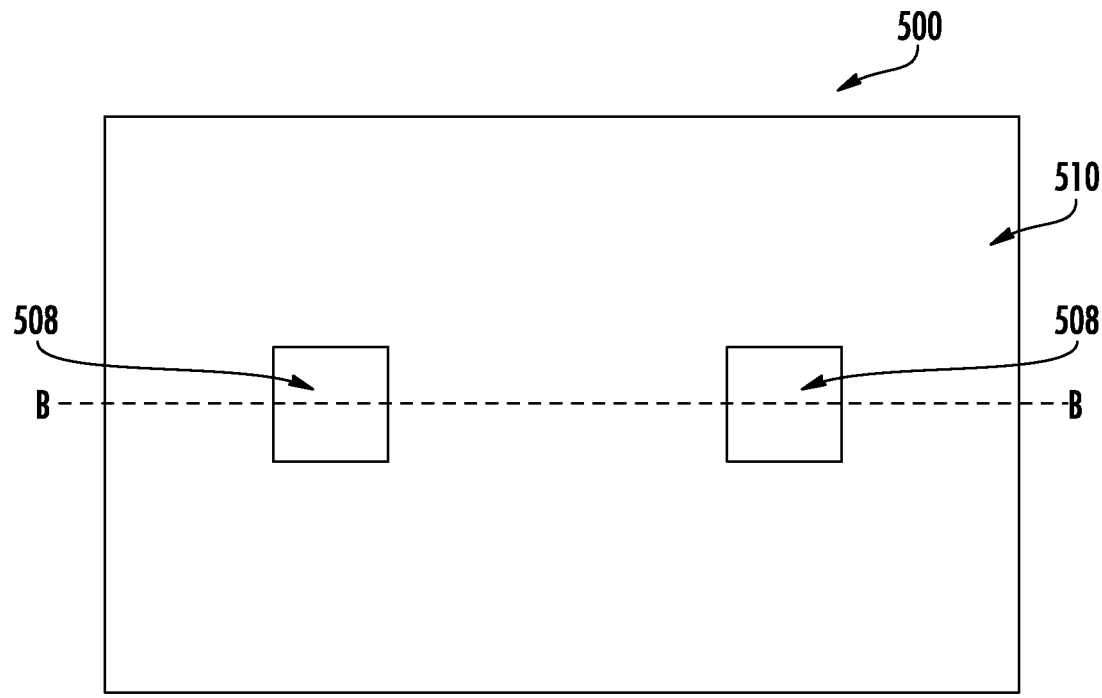
FIG. 5A illustrates a schematic diagram of a wireless stimulation device according to one embodiment described herein.
Figure 5B:
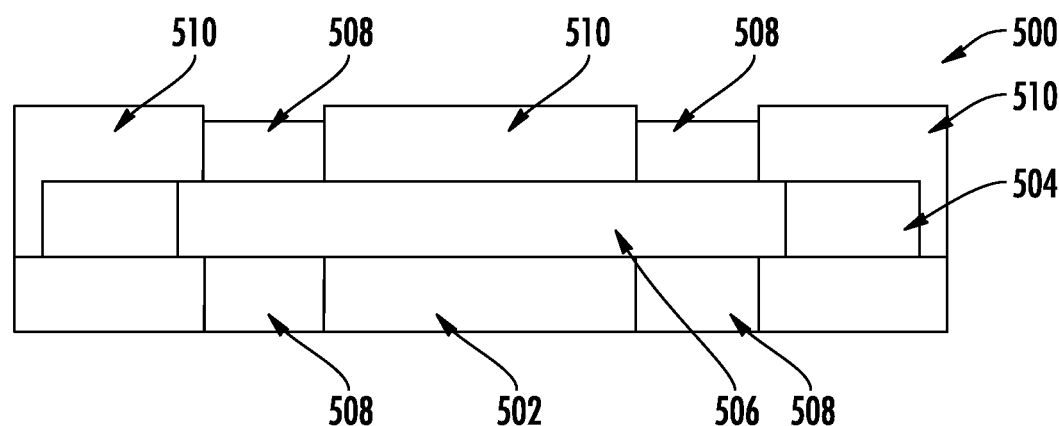
FIG. 5B illustrates a schematic diagram of a cross-sectional view of the wireless stimulation device of FIG. 5A taken along line B-B.

In a further embodiment, as illustrated in FIGS. 5A and 5B, a wirelessly powered muscular stimulation device (500) comprises a flexible or foldable substrate (502), at least one antenna (504) disposed on or defined by the flexible or foldable substrate (502), a circuit (506) disposed on or defined by the flexible or foldable substrate (502), electrodes (508), and a flexible or foldable superstrate (510) in facing opposition to the flexible or foldable substrate (502). As illustrated in FIGS. 5A and 5B, the substrate (502) and the superstrate (510) are in facing opposition to one another in a stacked configuration, such that the flexible or foldable substrate (502) defines a face that is substantially parallel, rather than substantially perpendicular, to a face defined by a side of the flexible or foldable superstrate (510). The antenna (504) is configured to receive an electromagnetic signal and to generate an electrical current from the electromagnetic signal. The electrodes (508) are operable to deliver the electrical current to a muscle in contact with a top surface of the device (500) and/or a bottom surface of the device (500). In the embodiment of FIGS. 5A and 5B, the circuit (502) comprises a capacitor (not shown), an inductor (not shown), and a controller (not shown). However, other components may also be used. FIG. 5A illustrates a top view of the device (500), and FIG. 5B illustrates a cross-sectional view of the device (500) taken along line B-B in FIG. 5A.

Turning now to specific components of devices, a wireless stimulation device described herein can comprise at least one circuit board. The circuit board can have any size, shape and/or configuration not inconsistent with the objectives of the present disclosure. For example, a circuit board or a device comprising a circuit board can be generally oblate or capsule shaped. A "capsule" shape, for reference purposes herein, can refer to a three-dimensional shape having an aspect ratio greater than one. Further, such a shape can have a small thickness relative to its length and width. Moreover, a capsule shape, in some embodiments, can have rounded corners or edges. Such a shape or configuration can, in some embodiments, permit facile implantation of the device in a patient, including by endoscopy. Other shapes are also possible. For example, a circuit board or a device comprising a circuit board can also be rectangular, square, oblong, or circular. Additionally, a circuit board described herein can have a circumference. A "circumference," for reference purposes herein, can comprise one or more curves and/or one or more straight line segments. Thus, a circumference need not be limited to a circular or rounded circuit board. Instead, a circumference can be defined by an outer periphery of the circuit board. In the case of a capsule shaped wireless device or circuit board, for instance, the circumference can be defined by the outer or exterior edges along the periphery of the device or board, such as along a rectangular, circular, or oblong perimeter. In the embodiment illustrated in FIG. 1, the circumference of the circuit board (102) lies in the plane defined by the arrow A.

A circuit board of a device described herein can also be formed from any material not inconsistent with the objectives of the present disclosure. In some cases, for instance, a circuit board comprises or is formed from one or more of glass, plastic, metal, or semiconductor material. A circuit board may also comprise or be formed from an organic polymer.

Further, in some embodiments, a wireless stimulation device described herein comprises a circuit disposed on a flexible or foldable substrate. In some such cases, the circuit is not disposed on a circuit board but is instead disposed on or defined by the flexible or foldable substrate itself. A circuit can be disposed on a flexible or foldable substrate in any manner not inconsistent with the objectives of the present disclosure. For example, in some cases, the circuit comprises or is formed from a metal deposited onto or patterned into the substrate to form connections, contacts, and/or other features. Such a deposition or patterning of a metal, in some instances, can be carried out using photolithography and/or etching. Moreover, it is also possible to place electronic components on the substrate. The electronic components can be placed on the substrate in any manner not inconsistent with the objectives of the present disclosure. In some instances, one or more electronic components are placed on the substrate through a butterfly connector. In some embodiments, the components are soldered. Alternatively, in other cases, the components are not soldered. An electronic component can also be surface mounted on the substrate, such by melting a copper, indium, or other bump on the surface of the substrate and placing the component on the bump.

A flexible or foldable substrate of a device described herein can be formed from any material not inconsistent with the objectives of the present disclosure. In some cases, for example, a flexible or foldable substrate comprises or is formed from a polymeric material, including a polymeric material for use in flexible electronic applications. In some instances, a flexible or foldable substrate comprises or is formed from a plastic. In some embodiments, a flexible or foldable substrate comprises or is formed from a polyimide. Other materials may also be used to form a flexible or foldable substrate. In addition, a flexible or foldable substrate can have any dimensions not inconsistent with the objectives of the present disclosure. For example, a flexible or foldable substrate described herein can have a thickness of less than about 500 µm, less than about 300 µm, or less than about 200 µm, where the "thickness" of a substrate can refer to the smallest dimension of the substrate or the dimension perpendicular to the plane of the antenna of the device. In some cases, a flexible or foldable substrate described herein has a thickness between about 50 µm and about 500 µm, between about 50 µm and about 300 µm, between about 50 µm and about 200 µm or between about 100 µm and about 150 µm. In some instances, the use of a substrate having a thickness recited above can permit the total thickness of the device to be small, including sufficiently small to permit the device to be disposed between tissue layers, such as between mucosal and submucosal tissue layers or between serosal and mucosal layers. In some embodiments, a device described herein can have a total thickness of less than about 5 mm, less than about 4 mm, less than about 3 mm, less than about 2 mm, less than about 1.5 mm, or less than about 1 mm. In some instances, a device described herein has a total thickness between about 0.5 mm and about 5 mm, between about 0.5 mm and about 4 mm, between about 0.5 mm and about 3 mm, between about 0.5 mm and about 2 mm, or between about 0.5 mm and about 1.5 mm. Other thicknesses are also possible. Moreover, the total thickness of a device described herein can be the sum of the substrate thickness (which, for example, may be about 50-150 µm), the height of any electronic components disposed on the substrate (which, for example, may be about 300-700 µm), and the total thickness of any biocompatible polymer coating disposed on or over the substrate and/or electronic components (which, for example, may be about 200-700 µm). In addition, a device having such a total thickness, in some cases, can also have a total length and/or width of less than about 3 cm, less than about 2 cm, less than about 1.5 cm, or less than about 1 cm. In some embodiments, such a device has a total length and/or total width of about 0.5 cm to about 3 cm, about 0.5 cm to about 2 cm, or about 1 cm to about 2 cm.

Further, a "foldable" substrate, for reference purposes herein, can be foldable so as to permit the substrate to be rolled or folded upon itself and subsequently unrolled and unfolded without breaking, and/or deformable so as to permit the substrate to undergo a change in shape with muscular or gastrointestinal tissue when the muscle or gastrointestinal tissue undergoes elastic deformation. Moreover, in some cases, a foldable substrate can have the same or substantially the same flexibility as muscle or gastrointestinal tissue, including mucosal tissue or submucosal tissue, in at least two dimensions. A substrate having "substantially" the same flexibility as a tissue can have a flexibility that is within about 20%, within about 15%, within about 10%, within about 5%, or within about 1% of the flexibility of the tissue, the percentage being based on the larger flexibility value. Further, it is to be understood that the flexibility of a tissue or substrate can be measured in any manner not inconsistent with the objectives of the present disclosure, such as a method consistent with ASTM D4338. In addition, in some embodiments, a flexible or foldable substrate described herein can be folded or deformed into a wrinkled, corrugated, or undulating configuration without breaking. Further, in some instances, a flexible or foldable substrate can be folded and unfolded, rolled and unrolled, or otherwise deformed and undeformed a plurality of times without breaking, such as at least 50 times, at least 100 times, or at least 1000 times. A foldable substrate described herein, in some cases, may also be expandable and/or thin so as to permit insertion of the substrate in or under a layer of muscle and/or gastrointestinal tissue, such as in a mucosal, submucosal, or serosal tissue region or in between submucosal tissue layers. Additionally, in some embodiments, a foldable substrate described herein is not elastic in the plane of the antenna of the device. Further, in some instances, a foldable substrate described herein has a Young's modulus of about 200 MPa to about 300 MPa or about 230 MPa to about 250 MPa, including when measured according to ASTM D638.

Further, it is to be understood that a flexible or foldable superstrate, when used, may have the same properties as a flexible or foldable substrate described herein. Moreover, in some embodiments, the use of a flexible or foldable substrate and/or superstrate can permit the entire wireless stimulation device to be flexible, conformable, deformable, and/or foldable in a manner described hereinabove.

Wireless stimulation devices described herein also comprise at least one antenna operable to receive an electromagnetic signal and to generate an electrical current from the electromagnetic signal. The antenna can comprise or be formed from any material not inconsistent with the objectives of the present disclosure. For example, in some embodiments, an antenna comprises or is formed from metal wire. Moreover, an antenna described herein can have any size, shape, or configuration not inconsistent with the objectives of the present disclosure. For example, in some embodiments, an antenna is wrapped around the circumference of a circuit board, as described hereinabove. In some cases, an antenna is wrapped around the circumference of the circuit board a plurality of times, including in a manner that the antenna does not overlap or overlay itself, thereby resulting in multiple antenna loops having substantially the same diameter. An antenna can also be wrapped around the circumference of a circuit board in a manner such that subsequent antenna loops have an increasing diameter relative to prior antenna loops. Further, in some cases, wrapping an antenna around the circumference of a circuit board in a manner described herein can permit the cross-sectional area of the antenna to be the same as, substantially the same as, or even greater than the cross-sectional area of the circuit board around which the antenna is wrapped. Areas that are "substantially" the same, for reference purposes herein, can be within about 5% or within about 10% of each other, based on the larger area. For example, in some cases, the cross-sectional area of the antenna is at least about 90%, at least about 95%, or at least about 99% of the cross-sectional area of the face of the circuit board around which the antenna is wrapped. In some instances, the cross-sectional area of the antenna is between about 90% and about 110% or between about 95% and about 105% of the cross-sectional area of the face of the circuit board around which the antenna is wrapped. It is to be understood that the "cross-sectional area" of an antenna or circuit board, for reference purposes herein, can refer to the area enclosed by the wrapped antenna and/or circuit board circumference. Additionally, in some devices, such as those comprising a flexible substrate, an antenna can be directly formed or placed in or on the substrate in a spiral configuration, including in a manner described hereinabove for the circuit of a flexible substrate. Providing an antenna in a manner described herein, in some instances, can maximize the antenna cycle or antenna loop diameter of a device without increasing or substantially increasing the total cross-sectional size of the device.

Wireless stimulation devices described herein also comprise at least one electrode operable to deliver electrical current to a muscle. The electrodes of a device described herein can have any size, shape, or configuration not inconsistent with the objectives of the present disclosure. In addition, any desired number of electrodes may be used. For example, in some embodiments, a wireless stimulation device can comprise at least two electrodes. Further, in some cases, the at least two electrodes are located on opposing ends of the device, such as in the embodiment of FIG. 1. Moreover, in some embodiments, one or more electrodes are generally loop shaped. Other configurations are also contemplated. For example, one or more electrodes of a device described herein can be plate shaped, rod shaped, coil shaped, ring shaped, or bent at an angle. In certain other embodiments, such as those comprising a flexible substrate, one or more electrodes can be generally perpendicular to the flexible substrate. Such configurations can permit electrode contact on a top and/or bottom surface of the device. More generally, it is also possible, in some instances, for one or more electrodes to be configured such that the one or more electrodes can provide electrical contact with muscle or other tissue on both a top surface and a bottom surface of a device, as illustrated, for example, in FIGS. 4A and 4B and FIGS. 5A and 5B.

In addition, the electrodes of a device described herein can comprise or be formed from any material and not inconsistent with the objectives of the present disclosure. In some cases, for instance, one or more electrodes comprise or are formed from a metal such as copper, silver, or gold. Other materials may also be used.

Wireless stimulation devices described herein also comprise at least one circuit. In some embodiments, at least one circuit is a charging circuit operable to provide electrical current to a rechargeable battery sufficient to charge the battery to an operating voltage. In certain other instances, at least one circuit is an energy harvesting circuit operable to receive electrical current from at least one antenna and to modify, amplify, or otherwise manipulate the electrical current to provide a current operable to stimulate muscle and/or gastrointestinal tissue. In some cases, such a circuit is a resonant circuit, such as an inductor-capacitor circuit. In generally, a circuit described herein can comprise, consist, or consist essentially of any components or elements not inconsistent with the objectives of the present disclosure. For example, in some cases, a circuit comprises a capacitor, an inductor, a regulator, and a controller.

A "capacitor," for reference purposes herein, is a passive two-terminal electrical component used to store energy electrostatically in an electric field. Capacitor designs vary, and any capacitor design not inconsistent with the objectives of the present disclosure may be used in a device described herein. For example, in some cases, a capacitor is a fixed capacitor. In other cases, a capacitor is a polarized capacitor. In some embodiments, a capacitor of a device described herein comprises at least two electrical conductors separated by a dielectric material such as glass, ceramic, plastic film, air, paper, and/or mica. Other capacitor structures may also be used.

A "regulator," for reference purposes herein, can be used to automatically maintain a constant voltage level. Any regulator not inconsistent with the objectives of the present disclosure can be used. For example, in some cases, a regulator is a low-dropout ("LDO") regulator. An LDO can be a DC linear voltage regulator which can operate with a very small input-output differential voltage. In some embodiments, an LDO comprises a power field-effect transistor and a differential amplifier. Such a configuration may be operable, upon the output voltage rising too high relative to a reference voltage, to maintain a constant output voltage via the power field-effect transistor. Other regulators may also be used in a device described herein.

A "controller," for reference purposes herein, can be used to automate control of stimulation or operation modes of a muscular stimulation device described herein. Any controller not inconsistent with the objectives of the present disclosure may be used. For example, in some cases, a controller comprises a microcontroller, such as a peripheral interface controller ("PIC"). Such a controller can have any processing, memory, and programmability constraints not inconsistent with the objectives of the present disclosure. For example, in some embodiments, the controller is operable to control at least 3 different operation or stimulation modes. Moreover, in some instances, the controller can be wirelessly reconfigured to permit variation or adjustment of operation or stimulation modes of the wireless muscular stimulation device, as described further hereinbelow.

Other components or features in addition to a capacitor, regulator, or controller may also be included in a circuit described herein. For example, in some cases, a circuit of a wireless muscular stimulation device described herein further comprises a charge pump. A "charge pump," for reference purposes herein, is a DC to DC converter that uses capacitors as energy storage elements to create either a higher or lower voltage power source. In some embodiments, a charge pump is utilized in a wireless muscular stimulation device to amplify voltage to a desired level for an operation or stimulation mode of the device from an input voltage based on received electromagnetic signals. Further, in some cases, a circuit of a wireless stimulation device described herein comprises a diode bridge. A "diode bridge," for reference purposes herein, is an arrangement of four or more diodes in a bridge circuit configuration that provides the same polarity of output for either polarity of input. In some embodiments, the use of a diode bridge can permit the conversion of alternating current input into a direct current output. In some such embodiments, the diode bridge may be referred to as a bridge rectifier.

Figure 6:
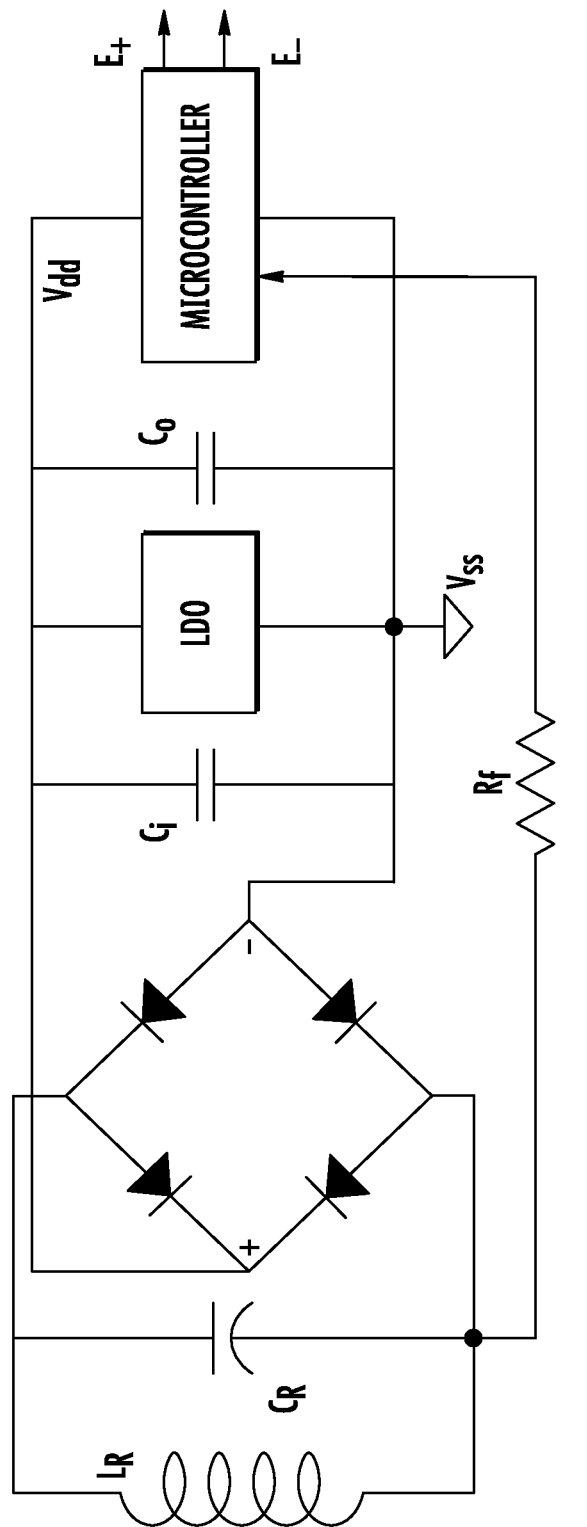
FIG. 6 illustrates a circuit diagram of a wireless stimulation device according to one embodiment described herein.

One embodiment of a circuit used in a wireless muscular stimulation device described herein is illustrated in FIG. 6. In the embodiment of FIG. 6, the wireless muscular stimulation device comprises an inductor-capacitor circuit operable to harvest electromagnetic signals to generate an electrical current, followed by a bridge rectifier and an LDO operable to power the microcontroller. Electrical current can be delivered through the electrodes by the microcontroller to the muscle and/or gastrointestinal tissue to be stimulated by the device. Other circuit structures may also be used in a wireless stimulation device described herein.

Wireless muscular stimulation devices described herein, in some embodiments, can also comprise one or more detectors or sensors. For example, in some cases, a wireless stimulation device described herein further comprises at least one pH sensor. Such a sensor may be operable to determine changes in pH in gastrointestinal tissue, and may be connected to a controller in such a manner that the controller can initiate or cease an operation or stimulation mode of the device based on preset or predetermined pH settings. In certain embodiments, for instance, a pH sensor is operable to detect pH changes associated with predetermined amounts of undigested food in a gastrointestinal environment.

In addition, in some cases, a wireless muscular stimulation device described herein further comprises a strain detector. A strain detector, in some embodiments, is operable to detect deformation of a gastrointestinal muscle or other muscle or tissue. Further, a strain detector can be in communication with a controller, thereby enabling automatic initiation or ceasing of an operation or stimulation mode of a device when a predetermined strain threshold is crossed. For example, in some cases, a strain detector may indicate the beginning or end of a digestion event, and may enable or cease an operation or stimulation mode of the device.

In addition, in some embodiments, one or more components of a wireless muscular stimulation device described herein are coated with a biocompatible polymer. A "biocompatible" polymer, for reference purposes herein, can refer to a polymer that is biocompatible according to one or more ISO 10993 standards. For example, a biocompatible polymer can be a polymer that is non-toxic and does not cause substantial tissue inflammation. Any biocompatible polymer not inconsistent with the objectives of the present disclosure may be used. In some cases, a biocompatible polymer comprises a synthetic polymer. In other instances, a biocompatible polymer comprises a naturally occurring polymer. Non-limiting examples of biocompatible polymers suitable for use in some embodiments of devices described include polydimethylsiloxane (PDMS), polyvinylchloride (PVC), polytetrafluoroethylene (PTFE), polyethersulfone (PES), polysulfone (PS), polyethylene (PE), polypropylene (PP), polyetheretherketone (PEEK), and polylactic acid (PLA) polymers. Other biocompatible polymers may also be used. In some cases, one or more of a circuit and/or a circuit board, antenna, rechargeable battery, switch, flexible substrate, and flexible superstate are coated with a biocompatible polymer described herein. However, in some embodiments, one or more electrodes of a device are not coated with a biocompatible polymer. Additionally, in some instances, a wireless muscular stimulation device described herein is coated entirely in a biocompatible polymer with the exception of at least one electrode. Moreover, it is to be understood that one or more components of a device can be coated with a biocompatible polymer individually or collectively. Further, a device or component of a device that is "coated" with a biocompatible polymer, for reference purposes herein, can have a surface that is completely or substantially completely covered by the polymer. For example, in some cases, up to about 99%, up to about 95%, or up to about 90% of the surface is covered, based on the total surface area of the surface. In other instances, between about 60% and about 100%, between about 70% and about 100%, between about 80% and about 100%, between about 85% and about 100%, between about 90% and about 100%, between about 90% and about 99%, or between about 95% and about 100% of a "coated" surface is covered by the biocompatible polymer.

II. Wireless Stimulation Systems

In another aspect, wireless stimulation systems such as wireless gastrointestinal stimulation systems are described herein. In some embodiments, a wireless gastrointestinal stimulation system comprises at least one transmitter and at least one stimulation device operable to deliver a pattern of electrical pulses to a gastrointestinal tissue. The gastrointestinal tissue can comprise a muscle. A transmitter of the system can comprise a signal generator operable to generate an electromagnetic signal, a first antenna operable to broadcast the electromagnetic signal, and an energy source. A stimulation device of the system can comprise any stimulation device described hereinabove in Section I. For example, in some cases, a stimulation device comprises a circuit board having a circumference, at least one second antenna wrapped around the circumference of the circuit board, the at least one second antenna being configured to receive the electromagnetic signal and to generate an electrical current from the electromagnetic signal, and at least one electrode operable to deliver the electrical current to the muscle or other tissue. Further, in some instances, at least one stimulation device comprises a battery, such as a rechargeable battery. In other embodiments, at least one stimulation device does not comprise a battery.

In addition, any number of stimulation devices not inconsistent with the objectives of the present disclosure can be used in a system described herein. In some cases, for instance, a system comprises at least two stimulation devices operable to deliver at least two patterns of electrical pulses to the gastrointestinal tissue. In other cases, a system comprises at least three or at least four stimulation devices. It is to be understood that embodiments comprising at least two (or n) stimulation devices can be operable to produce at least two (or n) patterns of electrical pulses. The patterns of electrical pulses can be the same or different, where "different" or "differing" patterns can have differing currents, voltages, powers, and/or temporal "on" and "off" periods. Thus, a system described herein, in some cases, can permit a wide variety of treatments to be performed on a patient. For example, in some embodiments, a plurality of individual stimulation devices can become operable (or "turn on" to provide electrical stimulation to tissue) when placed in proximity to a transmitter generating an electromagnetic signal in a carrier range at which the individual stimulation devices are configured to receive electromagnetic energy. In some instances, the plurality of devices can all receive an electromagnetic signal at the same frequency. Thus, in such cases, selection of which device or devices is in an "on" or operating mode can be based on the location of the transmitter relative to the devices. Alternatively, in other cases, different stimulation devices operate at different carrier frequencies and can thus be operated singly or in unison by transmission of varying carrier signals. More generally, the patterns of electrical pulses provided by a plurality of devices in a manner described herein can be the same or different from one another. For example, in some instances, at least three devices are used, and each individual device is configured to deliver a "low," "medium," or "high" degree or pattern of electrical stimulation to a tissue. Thus, in some such embodiments, a first stimulation device can be configured to provide a low amount of electrical stimulation, a second stimulation device can be configured to provide a medium amount of electrical stimulation, and a third stimulation device can be configured to provide a high amount of electrical stimulation. Further, each of the first, second, and third devices can be configured to provide its specified amount of electrical stimulation to a tissue based on the location of a single transmitter relative to each device and/or based on a varying carrier signal provided by a single transmitter of the system. Other configurations of the components of a system described herein are also possible. It is to be understood that various operation modes, such as modes corresponding to a "low," "medium," or "high" degree or pattern of electrical stimulation to a tissue, may differ in one or more of pulse amplitude, pulse duration, pulse frequency, pulse sequence duration, and/or time between pulse sequences.

Figure 7A:
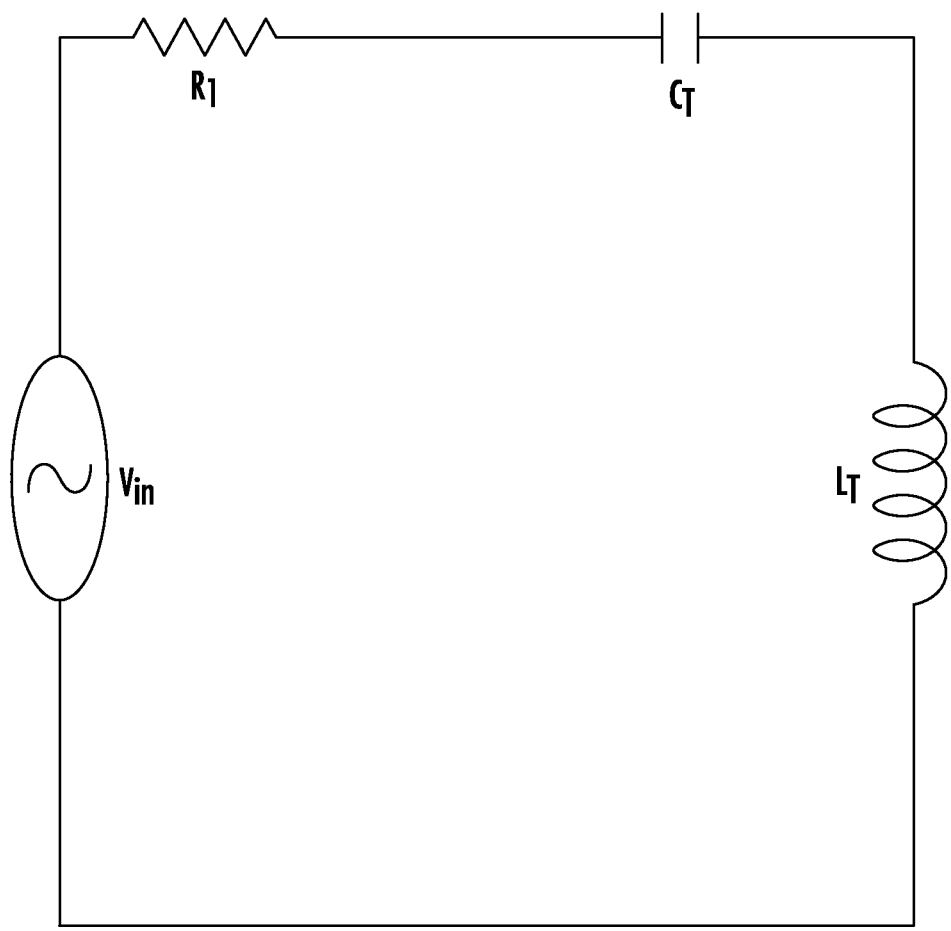
FIG. 7A illustrates a circuit diagram of a transmitter according to one embodiment of a wireless stimulation system described herein.
Figure 7B:
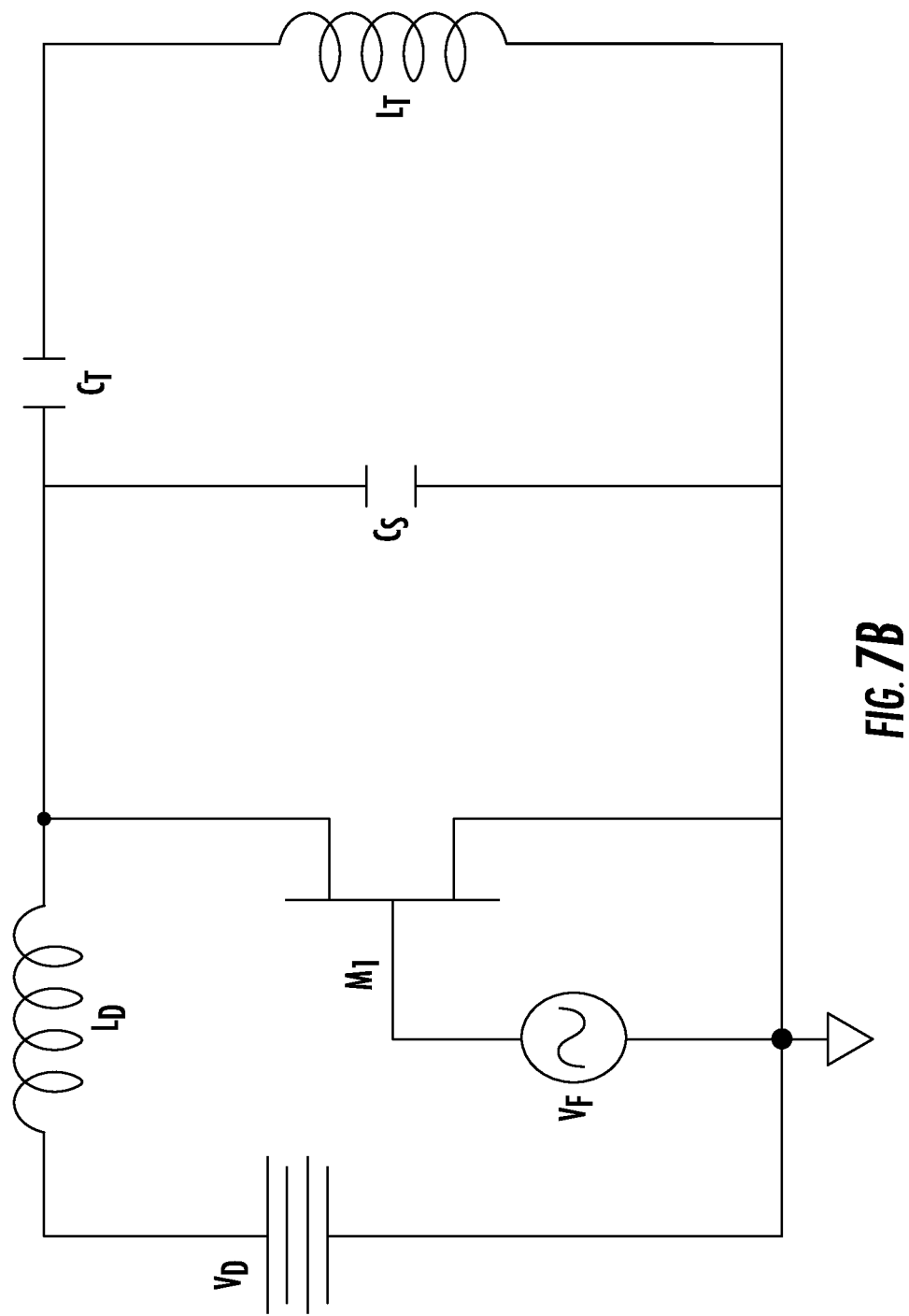
FIG. 7B illustrates a circuit diagram of a transmitter according to one embodiment of a wireless stimulation system described herein.

Turning again to the transmitter, wireless gastrointestinal stimulation systems described herein can comprise a single transmitter or more than one transmitter. Any transmitter not inconsistent with the objectives of the present disclosure may be used in a system described herein. For example, with reference to FIG. 7A, a transmitter is illustrated which comprises a signal generator operable to generate an electromagnetic signal, a first antenna operable to broadcast the electromagnetic signal, and an energy or power source. Any energy or power source not inconsistent with the objectives of the present disclosure may be used. For instance, a transmitter of a system described herein can be battery powered or powered through a connection to an electrical outlet, which may be a DC power source or an AC power source. In FIG. 7A, $L_T$ and $C_T$ represent a transmitter inductor-capacitor, or tank, circuit. Another embodiment of a transmitter described herein is illustrated schematically in FIG. 7B. The transmitter of FIG. 7B comprises an antenna, a signal generator, and an amplifier. Any amplifier not inconsistent with the objectives of the present disclosure can be used. For example, as illustrated in FIG. 7B, a class-E amplifier can be used to generate voltage across $L_T$ inductively linked by mutual inductance M with $L_R$. In the embodiment illustrated by FIG. 7B, adjustment of $L_T$ and $V_{dd}$ (positive supply voltage) from the battery is performed. Other configurations of stimulation systems described herein are also possible.

Moreover, in some cases, a transmitter of a stimulation system described herein is a wearable transmitter, such as a transmitter disposed in or attached to an article of clothing or a wearable therapeutic article such as a sling, harness, or brace. A "wearable" article, for reference purposes herein, can refer to an external article that can be worn by a patient, including a human patient, either as an article of clothing or as an accessory. In some embodiments, for instance, a wearable transmitter comprises a transmitter described herein disposed within, disposed on, or otherwise coupled to a sling, harness, brace, belt, jacket, or shirt in such a manner as to permit a wearer of the transmitter to use the transmitter to activate one or more stimulation devices of the system as needed or desired, including when the one or more stimulation devices are disposed or implanted within the body of the wearer.

III. Methods of Electrically Stimulating Gastrointestinal Tissue

In another aspect, methods of electrically stimulating gastrointestinal tissue in a patient are described herein. In some embodiments, a method of electrically stimulating gastrointestinal tissue in a patient comprises implanting at least one stimulation device in the patient, the at least one device comprising at least one second antenna configured to receive electromagnetic signals and to generate electrical current from the electromagnetic signals, and at least one electrode operable to deliver electrical current to the patient. The method further comprises transmitting an electromagnetic signal from a transmitter, the transmitter comprising an energy source, a signal generator, and a first antenna. The method also comprises receiving the electromagnetic signal with the second antenna of the stimulation device, generating an electrical current from the received electromagnetic signal, and delivering the electrical current through the at least one electrode to the patient.

Any stimulation device described hereinabove in Section I can be used in a method of electrically stimulating gastrointestinal tissue described herein. For example, in some embodiments, at least one stimulation device comprises a rechargeable battery. In such embodiments, the method can further comprise delivering the electrical current to the rechargeable battery after generating the electrical current in a recharging mode of the stimulation device and delivering the electrical current from the rechargeable battery to the at least one electrode in a stimulation mode of the stimulation device. Methods utilizing such devices can further comprise actuating a switch to switch between the recharging mode and the stimulation mode of the stimulation device.

Further, any transmitter described hereinabove in Section II can be used in a method of electrically stimulating gastrointestinal tissue described herein. For example, in some embodiments, the transmitter is external to the patient. Moreover, in some embodiments, the transmitter can be wearable.

In addition, a stimulation device described herein can be implanted in any manner not inconsistent with the objectives of the present disclosure. In some cases, the stimulation device is implanted endoscopically, including using an operating endoscope having a diameter of about 15 mm or less or about 10 mm or less. Further, in some such embodiments, an endoscopically implanted device can be implanted by disposing the endoscope through the mouth and esophagus of the patient and into the stomach of the patient. Moreover, in some instances, the stimulation device is a flexible or foldable device described herein, and the device is folded, rolled, or deformed to fit within the endoscope. Thus, in some cases, a device described herein is folded, rolled, or deformed into a size less than about 15 mm or less than about 10 mm. Further, in some such embodiments, the device is unfolded, unrolled, or undeformed following endoscopic implantation but prior to transmitting a signal from the transmitter, as described further hereinbelow. Other endoscopic implantation procedures may also be used in a method described herein.

Moreover, in some instances, the stimulation device is implanted within or adjacent to gastrointestinal tissue, muscle tissue, or other tissue. In some embodiments, for example, a stimulation device described herein is implanted in a submucosal region of a patient and/or in between submucosal layers, including in a gastrointestinal region of the patient. In certain other embodiments, a stimulation device described herein is implanted adjacent to or in contact with a mucosal layer, submucosal layer, and/or a serosal layer. In some instances, a stimulation device described herein is implanted between submucosal and mucosal layers of the stomach. In certain other cases, a stimulation device described herein can be implanted endoscopically, and at least one electrode can be deployed into a mucosal layer. In such embodiments, spring coils or endoscopic tacks can be used to enable transmural attachment of the device to the gastrointestinal tissue. In other instances, a stimulation device described herein is implanted in a patient without the use of tethers, clips, and/or sutures to contain the device, or without tethering, clipping, or suturing the device to tissue, such as tissue on the mucosal wall of the stomach of the patient. Instead, in some cases, the device is implanted in between tissue layers, such as mucosal, submucosal, and/or serosal tissue layers. Further, in some such instances, the tissue layers can be permitted to heal and/or rejoin to one another, thereby enclosing the device within the tissue. Implanting a stimulation device in a manner described herein, in some cases, can prevent the device from being pushed out of the patient or out of the implantation region of the patient, such as out of the stomach, due to biological activity within the patient, such as food digestion or the movement of solids and/or liquids within the stomach.

As described hereinabove, in some embodiments, a stimulation device can be implanted within or between submucosal layers or other tissue layers. Such implantation methods can be carried out in any manner not inconsistent with the objectives of the present disclosure, such as by incision of the tissue, expansion or displacement of the incised tissue, placement or implantation of the stimulation device, and replacement of the displaced or expanded tissue. In some such embodiments, a stimulation device described herein is implanted in a patient in a folded or rolled configuration and then subsequently unfolded or unrolled in vivo. Such a method of implanting a stimulation device can be particularly useful in embodiments comprising the use of a flexible stimulation device or a device having a flexible substrate. Stimulation devices may be implanted in a patient in other manners as well.

As described herein, implanting a stimulation device described herein in a patient and using the device to electrically stimulate gastrointestinal tissue of the patient can promote improved gastric motility and/or complete gastric emptying. Thus, in some cases, methods of electrically stimulating gastrointestinal tissue in a patient described herein can be carried out so as to alter or improve gastric motility. In some instances, the electrical current can be delivered to the patient in regular intervals over a period of minutes, hours, days, or weeks in order to alter digestive function and/or to improve gastric motility in a patient suffering from gastroparesis or other gastric dysmotility.

Moreover, as described hereinabove, implanting a stimulation device described herein in a patient and using the device to electrically stimulate tissue in a gastrointestinal region of the patient can promote appetite control and/or weight loss, including by inducing nausea in the patient. Further, in some instances, the electrical current can be delivered to the patient based on an amount of food consumed by the patient over a desired time period and/or based on the amount of food present in the digestive system of the patient at a desired point in time. Consistent with the foregoing description of devices provided hereinabove in Section I, one or more of a pH sensor and/or a strain sensor may be included in a stimulation device. A stimulation device including a pH sensor and/or a strain sensor can be used to measure pH within the digestive system and/or to measure elastic deformation of gastrointestinal tissue in order to initiate (or end) electrical stimulation or to signal an appropriate time to initiate (or end) electrical stimulation. In some such embodiments, a stimulation device including a pH sensor and/or a strain sensor may be operable to initiate (or end) a stimulation or operation mode independent of signal transmission control by the patient. In this manner, a patient can be prevented from interrupting or interfering with electric stimulation. Thus, in some embodiments, a method of treating obesity described herein comprises implanting a stimulation device described herein in the patient and delivering electric current to a gastrointestinal tissue of the patient using the stimulation device, wherein the electrical current is delivered to the gastrointestinal tissue based on a pH and/or strain detected by the implanted stimulation device.

In addition, delivering electric current to tissue in a manner described hereinabove can comprise delivering a plurality of pulses of electric current, including in a desired pattern or sequence, as opposed to delivering a non-pulsed or continuous current. Any pattern of pulses not inconsistent with the objectives of the present disclosure may be used. In some embodiments, for instance, a pulsed electrical current of a given total power or total current has a high frequency but a low current, as opposed to a low frequency and a high current. In some instances, for example, the pulse frequency is at least about 10 Hz, at least about 20 Hz, at least about 30 Hz, or at least about 50 Hz. In some embodiments, the pulse frequency is between about 10 Hz and about 100 Hz, between about 10 Hz and about 70 Hz, between about 10 Hz and about 60 Hz, or between about 10 Hz and about 40 Hz. Further, in some cases, a pulsed electric current described herein is delivered to tissue with a short pulse width and/or a low pulse duty cycle, such as a duty cycle of less than about 10%, less than about 5%, less than about 3%, less than about 2%, or less than about 1%. In some embodiments, the pulse duty cycle is between about 0.1% and about 10%, between about 0.1% and about 3%, between about 0.3% and about 5%, or between about 0.5% and about 2%. The pulse width, in some cases, is between about 200 µs and about 400 µs, between about 250 µs and about 350 µs, or between about 300 µs and about 350 µs. Delivering electric current to tissue, such as gastrointestinal or stomach tissue, in a manner described herein, in some embodiments, can provide adequate electrical stimulation of the tissue (such as for treating gastric dysmotility) without causing undesired tissue damage, pain, or discomfort in the patient, such as discomfort due to nausea.

IV. Methods of Reconfiguring a Wireless Stimulation Device

In another aspect, methods of reconfiguring a wireless stimulation device are described herein. Such methods can be used with devices having a resonant circuit operable to receive an electromagnetic signal transmitted within a carrier frequency range having a resonant frequency. In some embodiments, a method of reconfiguring a wireless stimulation device comprises transmitting a mode change signal to the device; transmitting a first data signal to the device, the first data signal comprising a first bit signal or a second bit signal; and transmitting a first confirmation signal to the device. The mode change signal has a frequency within a first band within the carrier frequency range, the first bit signal has a frequency within a second band within the carrier frequency range, the second bit signal has a frequency within a third band within the carrier frequency range, and the first confirmation signal has a frequency within a fourth band within the carrier frequency range. Moreover, the first band, second band, third band, and fourth band within the carrier frequency range can differ from one another. Differing bands, in some cases, do not have overlapping or substantially overlapping frequencies. Frequencies that do not "substantially" overlap, for reference purposes herein, can overlap by no greater than about 20%, no greater than about 15%, no greater than about 10%, no greater than about 5%, or no greater than about 1%, where the percentage is based on the width of the larger band. Further, power transfer efficiencies of the mode change signal, first data signal, and the first confirmation signal can vary less than about 5%, less than about 2%, less than about 1%, or less than about 0.5% from a power transfer efficiency of the resonant frequency, where the percentage is based on the power transfer efficiency of the resonant frequency.

A method described herein can be carried out using any transmitter and any wireless stimulation device not inconsistent with the objectives of the present disclosure. In some cases, for instance, a signal described herein is transmitted with a transmitter described hereinabove in Section II and received by a wireless stimulation device described hereinabove in Section I. Other transmitters and stimulation devices may also be used in a method described herein. In some embodiments, the wireless stimulation device of a method described herein comprises a resonant circuit comprising an LC inductor-capacitor circuit operable to receive an electromagnetic signal transmitted within a carrier frequency range, the carrier frequency range having a resonant frequency within the range. A "resonant frequency," for reference purposes herein, corresponds to a frequency or frequency range wherein the series impedance of an inductor and capacitor is at substantially a minimum and the parallel impedance is at substantially a maximum. Thus, a resonant frequency generally corresponds to a maximum power transfer efficiency of a device. Although a resonant circuit of a device may be configured or tuned to a particular resonant frequency, certain embodiments of devices described herein are operable to receive a carrier frequency shifted from the resonant frequency within a carrier frequency range without a significant drop in power coupling between the transmitter and the resonant circuit. A method described herein can be carried out using any carrier frequency range not inconsistent with the objectives of the present disclosure. In some embodiments, the carrier frequency range spans less than about 100 kHz, less than about 75 kHz, less than about 50 kHz, or less than about 25 kHz. Moreover, in some cases, the carrier frequency range is about 1.28 MHz to about 1.32 MHz or about 1.25 MHz to about 1.29 MHz. Other carrier frequency ranges may also be used in a method described herein.

Further, methods described herein can, in some cases, be carried out by stimulation devices having a finite quality factor of resonance configured for a desired carrier frequency range around a predetermined resonant frequency. "Quality factor," for reference purposes described herein, can refer to a parameter that describes a resonator's bandwidth relative to its resonant frequency. Stimulation devices described herein can be used which, in some embodiments, demonstrate a quality factor of resonance of less than about 200, less than about 150, or less than about 100. In some cases, a quality factor of resonance can be between about 10 and about 100, between about 20 and about 100, or between about 40 and about 100. In certain other cases, a quality factor of resonance can be between about 40 and about 200, between about 40 and about 150, or between about 40 and about 100. Moreover, in some embodiments, a quality factor of resonance can be used that is between about 20 and about 90, between about 40 and about 90, or between about 70 and about 90. Additionally, it is to be understood that quality factor may vary based on the resonant frequency used for a particular stimulation device described herein. For example, in embodiments utilizing a resonant frequency of about 1.3 MHz, a quality factor of resonance of between about 40 and about 100 can be used. In an embodiment utilizing a resonant frequency of about 6.7 MHz, a quality factor of resonance can be used between about 10 and about 70 or between about 20 and about 80.

A "mode change signal" of a method described herein, for reference purposes, can refer to a signal that conveys information to a device indicating that a mode change or reconfiguration operation is beginning, where a mode change or reconfiguration can refer to a change in the electrical stimulation to be provided by the device, as described further hereinabove. Further, a mode change signal, in general, can indicate to the stimulation device that one or more data signals are to follow, and that subsequent signals are to be stored in a controller disposed within the device. A "data signal" can refer to a signal that conveys information to a device regarding a desired electrical current output of the device. Further, a data signal can comprise, consist, or consist essentially of a bit signal (a "0" or a "1"). Thus, whether a data signal comprises a first bit signal (such as a 0) or a second bit signal (such as a 1) can determine one or more features of an electrical current output of a device.

As described herein, following the transmission and receipt of a mode change signal, one or more data signals can be transmitted to a device. Additionally, after a first data signal is sent or transmitted to the device, a first confirmation signal can be sent or transmitted to the device. A "confirmation signal" can refer to a signal that indicates that a prior data signal (or the bit signal value of the data signal) is to be stored in the device controller. The stored signal or value can then determine one or more features of the electrical current output of the device, unless and until further data signals are transmitted and received in a manner described hereinabove.

Figure 8:
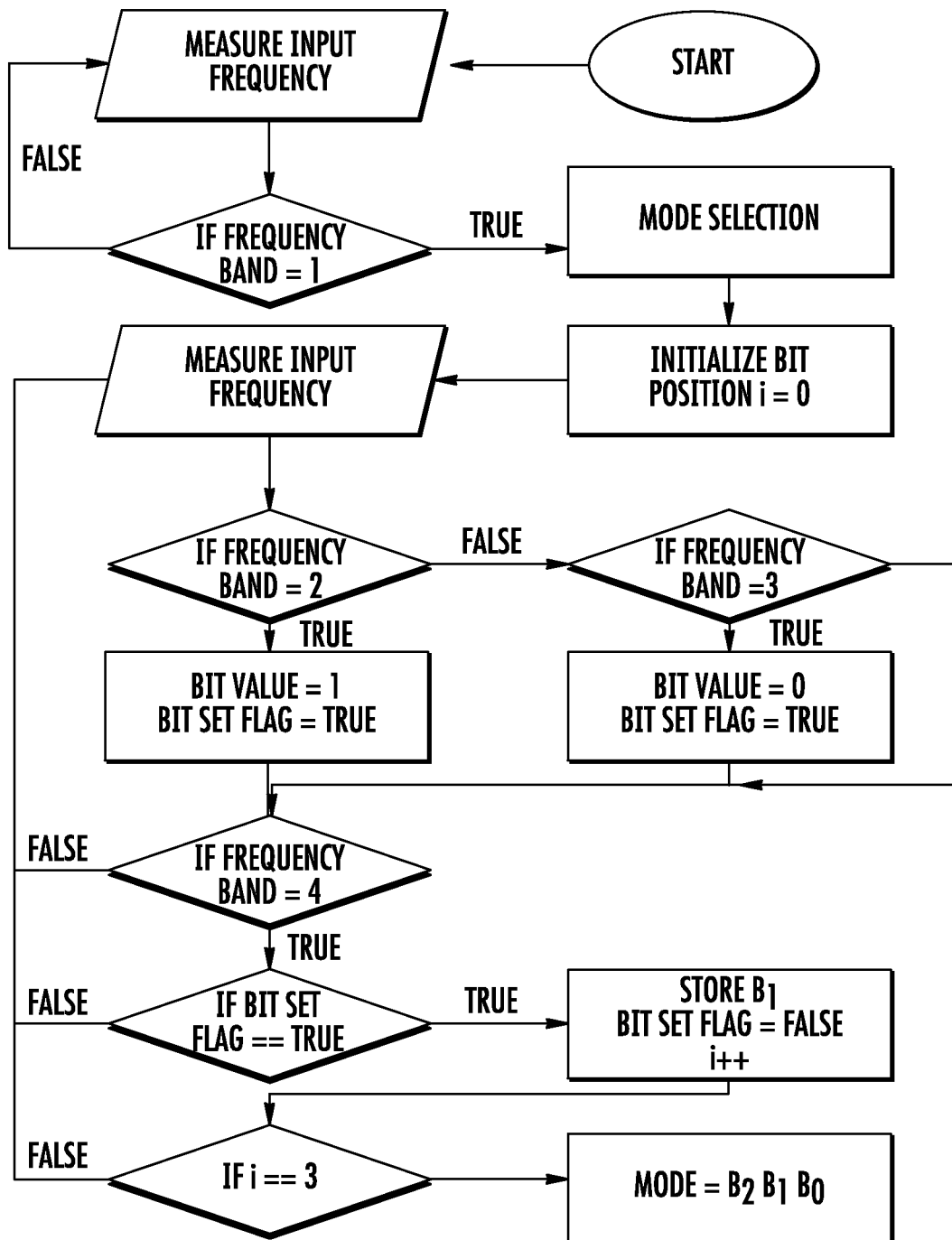
FIG. 8 illustrates schematically a method of reconfiguring a wireless stimulation device according to one embodiment described herein.

In some embodiments, a second (or nth) data signal can be further transmitted after the transmission and receipt of the first confirmation signal. For example, in some cases, a second data signal is sent or transmitted after the first confirmation signal, and a second confirmation signal is then sent or transmitted to indicate to the device that the second data signal is to be stored. In some such cases, the first data signal and the second data signal are the same, (i.e., both comprise 0 or both comprise 1). In other embodiments, the first data signal and the second data signal are not the same (i.e., the first and second data signals comprise 0 and 1, or 1 and 0, respectively). Further illustration of a method described herein is provided schematically in FIG. 8. In FIG. 8, the mode change signal is represented as band=1, the first bit signal is represented as band=2, the second bit signal is represented as band=3, and the first confirmation signal is represented as band=4.

Consistent with the foregoing description of the carrier frequency range, some embodiments of a method described herein comprise transmitting mode change signals, data signals, and confirmation signals all having a power transfer efficiency substantially the same as the resonant signal. For example, in some cases, the power transfer efficiencies of the mode change signal, first data signal, and the first confirmation signal vary less than 5%, less than 2%, less than 1%, or less than 0.5% from a power transfer efficiency of the resonant frequency. The power transfer efficiency can be determined according to Equation (1):

$$\eta = \frac{R_{load}}{R_{load} + R_{source}}, \tag{1}$$

wherein $\eta$ is the efficiency as a ratio of power dissipated by the load to power developed by the source, $R_{load}$ is the resistance across the electrodes and muscle or gastrointestinal tissue, and $R_{source}$ is the internal impedance of the device.

Some embodiments described herein are further illustrated in the following non-limiting examples.

Example 1

Wireless Stimulation Devices

Wireless stimulation devices according to some embodiments described herein were fabricated as follows. Specifically, a first device was a battery-powered, wirelessly rechargeable device corresponding to the block diagram illustrated in FIG. 2A. This device was denoted as a "wirelessly rechargeable stimulator" (WRS). The WRS included charge pump circuitry and a 3-V 11-mAh rechargeable battery. A magnetic reed switch connected the battery to the charging driver, or to a peripheral interface controller (PIC). The PIC was pre-programmed to generate electrical stimulation pulse trains with specific frequencies and duty cycles. The pulse trains were based on clinical investigation for muscle stimulation, and their specifications are shown in Table I below for "low," "medium," and "high" settings. In Table I, $T_p$ refers to the pulse width or duration of individual pulses within a pulse sequence, $T_o$ refers to the time between pulses during the during the sequence, and $T_{on}$ and $T_{off}$ refer to the on and off times of the sequence. The switch of the WRS was activated by an external magnet and was used to switch the mode of the device between a charging mode and an operating or stimulation mode.

The second device was a batteryless, wirelessly powered stimulation device corresponding to the block diagram illustrated in FIG. 3A. This device was denoted as a "batteryless wirelessly powered stimulator" (BWPS). The BWPS was configured to harvest electromagnetic energy received from a transmitter and to directly generate stimulation pulses from this received electromagnetic energy, without the use of a battery. The BWPS also included a PIC as described above, and the PIC was configured to turn the device off when the device received insufficient energy to provide a desired electrical current pattern, or when the transmitter was removed from the proximity of the patient. Both the WRS and the BWPS were fabricated on a miniature printed circuit board with a copper wire coil antenna having an American wire gauge (AWG) of 24 wrapped around the circumference of the circuit board in the manner illustrated in FIG. 1. The copper wire was wrapped around the circumference n times to provide an n-turn copper coil antenna. In the present Example, n was 14. However, in other cases, n was 10. In general, the number of turns n was selected for a given gauge of wire (e.g., AWG of 24) to maintain an overall device size sufficiently small for endoscopic implantation (such as a device thickness, length, or width described hereinabove). For instance, in some embodiments, a wire having an AWG of 26 or a litz wire was used. Wires having smaller diameters could be wrapped around the circumference of the circuit board a greater number of times to provide an n-turn coil antenna having a greater value of n without unduly increasing the overall device size. Higher values of n could provide a higher coupling efficiency between coils but could also alter the matching of capacitance for resonance. The devices were then coated with PDMS. Two uncoated metal wires extending from each device formed electrodes for delivering electric current to tissue.

Both wireless devices were powered by inductive coupling at 1.27 MHz and 4 W. The transmitter coil size used with both devices was 11.5×11.5 cm$^2$, and the transmitter coil was formed from litz wires or copper wire having an AWG of 24. The coil was driven by a class-E amplifier with a biasing voltage of 5 V and a 50% duty-cycle square waveform generated by a microprocessor.

TABLE I

Pulse Specifications.

| Setting | $T_p/T_o$ (μs/ms) | Pulse frequency (Hz) | Pulse duty cycle % | $T_{on}/T_{off}$ (s) | Number of pulses per cycle |
|---|---|---|---|---|---|
| Low | 330/71.4 | 14 | 0.46 | 0.1/5.0 | 2 |
| Medium | 330/35.7 | 28 | 0.92 | 1.0/4.0 | 28 |
| High | 330/18.2 | 55 | 1.82 | 4.0/1.0 | 216 |

Example 2

Methods of Stimulating Tissue

Methods of electrically stimulating tissue according to some embodiments described herein were carried out as follows. Specifically, to evaluate the WRS and BWPS stimulation devices of Example 1, an acute pig model was employed with approval from and following protocols established by the Animal Control Board of the University of Mississippi Medical Center. A 100-lb anesthetized pig was endoscopically implanted with two sets of unipolar myocardial stainless steel pacing leads, and the leads were attached serosally and mucosally. A neurostimulator device commonly known as ENTERRA® (available from Medtronic, Inc.) was used for comparison with the devices of Example 1.

To evaluate the control and experimental devices, each device was connected to the leads and a period of electrical signal recording was carried out as described below. Recordings at each stimulation setting (low, medium, and high) were made. The serosal DC impedance was measured as 1179Ω, while the mucosal DC impedance was measured as 594Ω.

First, the stimulators were placed outside of the body with wires connected to the stomach tissue. This condition was considered the in vitro condition. Next, the stimulators and wires were placed inside the body with the incision opening clip closed. This condition was considered the in vivo condition.

A data acquisition system was used to measure the voltage outputs of the stimulators, and the amount of electrical current delivered into the tissues was computed from the voltage readings and the measured DC impedances of the tissues. Mucosal and serosal EGG recordings were analyzed by signal averaging for mean frequencies and amplitudes, as well as the frequency-to-amplitude ratios (FARs). Results for the ENTERRA® control device and the WRS and BWPS devices are provided in Tables II-V.

TABLE II

Current delivered by the stimulators at low, medium and high does settings in the serosa.

| | WRS | | | | | |
|---|---|---|---|---|---|---|
| | Low | | Medium | | High | |
| Dose | In vitro | In vivo | In vitro | In vivo | In vitro | In vivo |
| Current | 1.70 mA | 1.70 mA | 1.93 mA | 1.93 mA | 1.93 mA | 1.93 mA |

| | BWPS | | | | | |
|---|---|---|---|---|---|---|
| | Low | | Medium | | High | |
| Dose | In vitro | In vivo | In vitro | In vivo | In vitro | In vivo |
| Current | 2.93 mA | 2.26 mA | 2.93 mA | 2.26 mA | 2.93 mA | 2.26 mA |

| | ENTERRA | | | | | |
|---|---|---|---|---|---|---|
| | Low | | Medium | | High | |
| Dose | In vitro | In vivo | In vitro | In vivo | In vitro | In vivo |
| Current | 5 mA* | 5 mA* | — | — | 8.9 mA | 8.9 mA |

*The ENTERRA® device behaves as a current source when used at the pre-set low setting. The device works as a voltage source when used at high settings.

TABLE III

Current delivered by the stimulators at low, medium and high dose settings in the mucosa.

| | WRS | | | | | |
|---|---|---|---|---|---|---|
| | Low | | Medium | | High | |
| Dose | In vitro | In vivo | In vitro | In vivo | In vitro | In vivo |
| Current | 3.45 mA | 3.45 mA | 3.63 mA | 3.63 mA | 3.63 mA | 3.63 mA |

| | BWPS | | | | | |
|---|---|---|---|---|---|---|
| | Low | | Medium | | High | |
| Dose | In vitro | In vivo | In vitro | In vivo | In vitro | In vivo |
| Current | 6.56 mA | 5 mA | 6.56 mA | 5 mA | 6.56 mA | 5 mA |

| | ENTERRA | | | | | |
|---|---|---|---|---|---|---|
| | Low | | Medium | | High | |
| Dose | In vitro | In vivo | In vitro | In vivo | In vitro | In vivo |
| Current | 5 mA* | 5 mA* | — | — | 17.7 mA | 17.7 mA |

*The ENTERRA® device works as a current source when used at the pre-set low setting. The device works as a voltage source when used at high settings.

TABLE IV

EGG signal summary for signals measured when electrodes were placed in serosa.

| Stimulator | Battery | Setting | Rhythm | Mean Freq. (Hz) | Freq Range (Hz) | Wave Amp. (V) | Mean Amp. (V) | Amp Range (V) | FAR (HzV$^{-1}$) |
|---|---|---|---|---|---|---|---|---|---|
| Control |  | OFF | RR | 3.67 | 3.0-4.0 | EA | 0.16 | 0.15-0.18 | 22.94 |
| ENTERRA | Non-rechargeable | Low | RR | 3.67 | 3.0-4.0 | EA | 0.18 | 0.18-0.19 | 20.39 |
| Low WRS #1 | Rechargeable | Low | RR | 3.50 | 3.0-4.0 | EA | 0.20 | 0.20-0.21 | 17.50 |
| WRS #2 | Rechargeable | Medium | RR | 3.08 | 3.0-3.3 | EA | 0.17 | 0.15-0.20 | 18.10 |
| WRS #3 | Rechargeable | High | RR | 3.75 | 3.5-4.0 | EA | 0.14 | 0.10-0.18 | 26.80 |
| BWPS #1 | Batteryless | Low |  | EGG was not recorded |  |  |  |  |  |
| BWPS #1 | Batteryless | Low | RR | 3.08 | 3.0-3.3 | EA | 0.07 | 0.05-0.09 | 44.00 |
| BWPS #2 | Batteryless | Medium | RR | 3.00 | 3.0-3.0 | EA | 0.14 | 0.12-0.15 | 21.43 |

TABLE V

EGG signal summary for signals measured when electrodes were placed in mucosa.

| Stimulator | Battery | Setting | Rhythm | Mean Freq. (Hz) | Freq Range (Hz) | Wave Amp. (V) | Mean Amp. (V) | Amp Range (V) | FAR (HzV$^{-1}$) |
|---|---|---|---|---|---|---|---|---|---|
| Control |  | OFF | RR | 3.00 | 3.0-3.0 | EA | 0.09 | 0.08-0.10 | 33.33 |
| BWPS #1 | Batteryless | Low |  | EGG was not recorded |  |  |  |  |  |
| BWPS #2 | Batteryless | Medium | RR | 3.00 | 3.0-3.0 | EA | 0.06 | 0.06-0.07 | 50.00 |
| BWPS #3 | Batteryless | High | RR | 3.83 | 3.0-5.0 | EA | 0.1 | 0.08-0.13 | 38.30 |

Example 3

Methods of Reconfiguring a Wireless Stimulation Device

A method of reconfiguring a wireless stimulation device according to one embodiment described herein was carried out as follows. A transmitting antenna coil and a receiving antenna coil were made and tuned to a carrier frequency range having a resonant frequency of 1.3 MHz. The carrier frequency range was divided into four bands, each frequency band representing certain information as shown in Table VI. Each band had a 10-kHz bandwidth and the overall bandwidth used for "coding" was only 40 kHz. Band #1 represents "Mode Change Operation." Band #4 represents "Confirmation Bit." Band #2 and Band #3 represent "Bit=1" and "Bit=0" as indicated in Table VI. The power transfer efficiency changed by less than 1% when the carrier frequency shifted away from the resonant frequency of 1.3 MHz within the range of 1.28-1.32 MHz.

TABLE VI

Frequency bands for information.

| Freq. Band | Freq. Range | Information |
|---|---|---|
| Band #1 | 1.32 MHz > f ≥ 1.31 MHz | Mode change operation |
| Band #2 | 1.31 MHz > f ≥ 1.3 MHz | Bit = '1' |
| Band #3 | 1.30 MHz > f ≥ 1.29 MHz | Bit = '0' |
| Band #4 | 1.29 MHz > f ≥ 1.28 MHz | Confirmation of a bit |

FIG. 8 shows the flow chart of logics in the microcontroller of the stimulator to determine the commands coded inside the wireless power transfer carrier signal. When an operator decides to change the stimulation setting, the transmitter coil is temporarily moved away from the patient, causing the implanted device to cease stimulation (in BWPS embodiments). Next, the transmitter coil is placed proximate to the patient again, and the microcontroller determines the incoming frequency. If the frequency is 1.3 MHz, the stimulator remains in the previous setting.

If a setting change is necessary, the carrier frequency in the transmitter is adjusted to Band #1 to indicate a mode change operation is imminent. Once the receiver coil receives the Band #1 signal, the microcontroller starts tracking the frequency information. The operator then changes the transmitter to either Band #2 or Band #3 in order to record a first bit as "1" or "0," respectively. The carrier frequency is then adjusted to Band #4 to confirm that a bit has been sent. If the transmitter then adjusts to Band #2 or Band #3, a second bit will be recorded as "1" or "0." Transmitting at Band #4 again will confirm the transmission of the second bit. Additional bits can be sent in the same manner as the second bit.

The microcontroller, after reception of the preconfigured number of bits, can determine the desired stimulator setting. The carrier frequency can then be returned to the resonant frequency of 1.3 MHz for wireless power transfer at maximum efficiency. A number, N, of bits can be used that ensures $2^N$ (in the foregoing case $2^2$ or 4) different modes of operation. In the case of 2 bits of "0" or "1," a set of stimulation modes can be used consistent with Table VII.

TABLE VII

Different modes as represented by three bits of information.

| Transmitted information | | |
|---|---|---|
| Bit 2 | Bit 1 | Mode |
| 0 | 0 | Low |
| 0 | 1 | Medium |
| 1 | 0 | High |

Example 4

Methods of Reconfiguring a Wireless Stimulation Device

A method of reconfiguring a wireless stimulation device according to one embodiment described herein was carried out as follows. Specifically, in this Example, the method of Example 3 was used with a gastrointestinal stimulation system including three stimulation devices. The microcontroller or PIC of each stimulation device could be coded with four bits. The first two bits (Bit 1 and Bit 2) corresponded to the identities of the devices, and the last two bits (Bit 3 and Bit 4) were mode change bits. In the case of the present example, a transmission of Bit 1="0" and Bit 2="0" corresponded to Implant 1; a transmission of Bit 1="1" and Bit 2="0" corresponded to Implant 2; and a transmission of Bit 1="0" and Bit 2="1" corresponded to Implant 3. When the transmitter adjusted the transmission carrier frequency among Bands #1-4, all devices received the carrier signals. Only when the transmitted bands matched with the preprogrammed bit information in the microcontroller of a specific device as indicated in the foregoing would the specific device be reconfigured accept the bit change operation. Once Bit 1 and Bit 2 were transmitted and individually confirmed by transmission of Band #4, Bit 3 and Bit 4 were transmitted via the method provided in Example 3 to designate the desired mode for the respective device.

This method can be used with as many implants as desired with only four frequency bands by variation only in the number of bits recorded. M+N bits can be used to provide for $2^M$ devices having $2^N$ settings each. For example, transmission of two implant identification bits (in this example Bit 1 and Bit 2) permits identification of $2^2$ or 4 separate implants, although only 3 implants were utilized. Transmission of 2 mode designation bits (in this example Bit 3 and Bit 4) permits designation of $2^2$ or 4 separate modes, although only 3 modes ("low," "medium," and "high") were utilized. Table VIII demonstrates information for three implants having three electrical current output settings (or "modes") each.

TABLE VIII

Different modes as represented by four bits of information.

| Bit 4 | Bit 3 | Bit 2 | Bit 1 | |
|---|---|---|---|---|
| 0 | 0 | 0 | 0 | Implant 1, Low |
| 0 | 1 | 0 | 0 | Implant 1, Medium |
| 1 | 0 | 0 | 0 | Implant 1, High |
| 0 | 0 | 0 | 1 | Implant 2, Low |
| 0 | 1 | 0 | 1 | Implant 2, Medium |
| 1 | 0 | 0 | 1 | Implant 2, High |
| 0 | 0 | 1 | 0 | Implant 3, Low |
| 0 | 1 | 1 | 0 | Implant 3, Medium |
| 1 | 0 | 1 | 0 | Implant 3, High |

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

That which is claimed is:

1. A method of electrically stimulating gastrointestinal tissue in a patient, the method comprising:
   implanting at least one stimulation device in the patient, the at least one stimulation device comprising at least one second antenna configured to receive electromagnetic signals and to generate electrical current from the electromagnetic signals, and at least one electrode in operable communication with the second antenna and configured to deliver the electrical current to gastrointestinal tissue of the patient based at least in part on the received electromagnetic signals;
   transmitting an electromagnetic signal from a transmitter, the transmitter comprising an energy source, a signal generator, and a first antenna;
   receiving the electromagnetic signal with the second antenna;
   generating, by the second antenna, an electrical current from the received electromagnetic signal; and
   delivering the electrical current through the at least one electrode to gastrointestinal tissue of the patient,
   wherein the at least one stimulation device is implanted between a mucosal layer and a submucosal layer of a stomach of the patient or between a submucosal layer and a serosal layer of a stomach of the patient.

2. The method of claim 1, wherein the at least one stimulation device is implanted endoscopically by disposing an endoscope through a mouth and esophagus of the patient and into the stomach of the patient.

3. The method of claim 1, wherein the electrical current is a pulsed electrical current having one or more of a pulse frequency between 10 Hz and 100 Hz, a pulse duty cycle between 0.1% and 3%, and a pulse width between 200 μs and 400 μs.

4. The method of claim 1, wherein the at least one stimulation device does not comprise a battery.

5. The method of claim 1, wherein the at least one stimulation device comprises a rechargeable battery, and the method further comprises:
   delivering the electrical current to the rechargeable battery after generating the electrical current in a recharging mode of the stimulation device;
   delivering the electrical current from the rechargeable battery to the at least one electrode in a stimulation mode of the stimulation device; and
   actuating a switch to switch between the recharging mode and the stimulation mode of the stimulation device.

6. The method of claim 1, wherein the transmitter is external to the patient.

7. The method of claim 1, wherein the at least one stimulating device comprises a resonant circuit operable to receive an electromagnetic signal transmitted within a carrier frequency range having a resonant frequency, and the method further comprises reconfiguring the stimulation device by:
   transmitting a mode change signal to the device from the transmitter;
   transmitting a first data signal to the device from the transmitter, the first data signal comprising a first bit signal or a second bit signal; and
   transmitting a first confirmation signal to the device from the transmitter,
   wherein the mode change signal has a frequency within a first band within the carrier frequency range;
   wherein the first bit signal has a frequency within a second band within the carrier frequency range;
   wherein the second bit signal has a frequency within a third band within the carrier frequency range;

wherein the first confirmation signal has a frequency within a fourth band within the carrier frequency range; and wherein power transfer efficiencies of the mode change signal, first data signal, and the first confirmation signal vary less than 1% from a power transfer efficiency of the resonant frequency.

8. The method of claim 7 further comprising transmitting a second data signal to the device from the transmitter and transmitting a second confirmation signal to the device from the transmitter.

9. The method of claim 8, wherein the first data signal and the second data signal are the same.

10. The method of claim 8, wherein the first data signal and the second data signal are different.

11. The method of claim 7, wherein the carrier frequency range spans less than about 50 kHz.

12. The method of claim 7, wherein the carrier frequency range is about 1.28 MHz to about 1.32 MHz.

13. The method of claim 7, wherein the carrier frequency range is about 1.25 MHz to about 1.29 MHz.

14. The method of claim 1, wherein the second antenna is disposed on a foldable substrate of the at least one device.

15. The method of claim 7, wherein:
the second antenna and the circuit are disposed on a foldable substrate of the device; and
the second antenna and the circuit are separate components of the device.

16. The method of claim 14, wherein the foldable substrate can be rolled upon itself and subsequently unrolled without breaking.

17. The method of claim 14, wherein the foldable substrate has a flexibility that is within 20% of a flexibility of the gastrointestinal tissue, the percentage being based on the larger flexibility value.

18. The method of claim 1, wherein the electrical current is delivered to a muscle.

19. The method of claim 18, wherein, the electrical current is delivered to the muscle through both a top surface and a bottom surface of the device.

20. The method of claim 1, wherein:
the device further comprises a pH detector or a strain detector; and
the method further comprises measuring a pH or a strain of the gastrointestinal tissue with the pH detector or the strain detector.

* * * * *